(12) United States Patent
Meyers et al.

(10) Patent No.: US 6,849,437 B2
(45) Date of Patent: Feb. 1, 2005

(54) 47153, A HUMAN GLYCOSYLTRANSFERASE FAMILY MEMBER AND USES THEREFOR

(75) Inventors: Rachel Meyers, Newton, MA (US); Julie Beth Rosenfeld, Sharon, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/113,709

(22) Filed: Mar. 28, 2002

(65) Prior Publication Data

US 2004/0248242 A1 Dec. 9, 2004

Related U.S. Application Data

(60) Provisional application No. 60/279,647, filed on Mar. 28, 2001.

(51) Int. Cl.[7] .......................... C07H 21/04; C12N 9/00; C12N 9/10; C12N 1/20; C12N 5/00
(52) U.S. Cl. ............................... 435/193; 435/4; 435/6; 435/69.1; 435/252.3; 435/320.1; 435/325; 435/350; 435/351 T; 435/354 T; 435/358; 435/364; 435/365; 530/350 T; 536/23.2; 536/23.4; 536/23.5
(58) Field of Search ................................ 435/4, 6, 69.1, 435/183, 193, 252.3, 320.1, 325 T, 350 T, 351, 354, 358, 364, 365, 41; 530/350; 536/23.2–23.7

(56) References Cited

U.S. PATENT DOCUMENTS

2003/0236392 A1 12/2003 Isogai et al.

OTHER PUBLICATIONS

Sulston et al. GenBank Database accession No. AC006017, Dec. 21, 1999.*
Strausberg, R. L., et al., "*Homo Sapiens* UDP–N–acetyl–alpha–D–galactosamine:polypeptide N–acetylgalactosaminyltransferase 15, mRNA (cDNA clone MGC:26636 IMAGE:4825619), complete cds.", Jun. 30, 2004 (sequence) GenBank [online] Bethesda, MD, USA: National Center for Biotechnology Information [retrieved on Jul. 20, 2004]. Retrieved from the internet: GenBank Accession No. BC022021.
Hashimoto, K. et al., "Macaca Fascicularis Testis cDNA Clone:QtsA–12718, full insert sequence", Aug. 16, 2001 (sequence) GenBank [online] Bethesda, MD, USA: National Center for Biotechnology Information [retrieved on Jul. 20, 2004]. Retrieved from the internet: Genbank Accession No. AB070053.
Hashimoto, K. et al., "Macaca Fascicularis Testis cDNA Clone:QtsA–11465, full insert sequence", Feb. 22, 2003 (sequence) GenBank [online] Bethesda, MD, USA: National Center for Biotechnology Information [retrieved on Jul. 20, 2004]. Retrieved from the internet: Genbank Accession No. AB070020.

(List continued on next page.)

*Primary Examiner*—Manjunath N. Rao
(74) *Attorney, Agent, or Firm*—Millennium Pharmaceuticals, Inc.

(57) ABSTRACT

The invention provides isolated nucleic acids molecules, designated 47153 nucleic acid molecules, which encode novel glycosyltransferase family members. The invention also provides antisense nucleic acid molecules, recombinant expression vectors containing 47153 nucleic acid molecules, host cells into which the expression vectors have been introduced, and nonhuman transgenic animals in which a 47153 gene has been introduced or disrupted. The invention still further provides isolated 47153 proteins, fusion proteins, antigenic peptides and anti-47153 antibodies. Diagnostic and therapeutic methods utilizing compositions of the invention are also provided.

11 Claims, 8 Drawing Sheets

OTHER PUBLICATIONS

Strausberg, R. L., et al., "*Homo Sapiens* UDP–N–acetyl–alpha–D–galactosamine:polypeptide N–acetylgalactosaminyltransferase 15, mRNA (cDNA clone IMAGE:4831104), containing frame–shift errors", Nov. 19, 2003 (sequence) GenBank [online] Bethesda, MD, USA: National Center for Biotechnology Information [retrieved on Jul. 20, 2004]. Retrieved from the internet: Genbank Accession No. BC025391.

Oshima, A., et al., "*Homo Sapiens* cDNA FLJ35772 fis, clone TESTI2005120, weakly similar to POLYPEPTIDE N–ACETYLGALACTOSAMINYLTRANSFERASE (EC 2.4.1.41)", Jan. 30, 2004 (sequence) GenBank [online] Bethesda, MD, USA: National Center for Biotechnology Information [retrieved on Jul. 20, 2004]. Retrieved from the internet: GenBank Accession No. AK093091.

Hashimoto, K. et al., "Macaca Fascicularis Testis cDNA Clone:QtsA–10105, full insert sequence", Aug. 16, 2001 (sequence) GenBank [online] Bethesda, MD, USA: National Center for Biotechnology Information [retrieved on Jul. 20, 2004]. Retrieved from the internet: Genbank Accession No. AB069985.

Guo, J. H., et al., "*Homo Sapiens* unknown mRNA", Jul. 23, 2003 (sequence) Genbank [online] Bethesda, MD, USA: National Center for Biotechnology Information [retrieved on Jul. 20, 2004]. Retrieved from the internet: Genbank Accession No. AF440404.

Guo, J. H., et al., "*Homo Sapiens* unknown mRNA", May 01, 2002 (sequence) Genbank [online] Bethesda, MD, USA: National Center for Biotechnology Information [retrieved on Jul. 20, 2004]. Retrieved from the internet: Genbank Accession No. AF440400.

Strausberg, R. L., et al., "UDP–N–acetyl–alpha–D–galactosamine:polypeptide N–acetylgalactosaminyltransferase 15 [*Homo Sapiens*]", Jun. 30, 2004 (sequence) GenBank [online] Bethesda, MD, USA: National Center for Biotechnology Information [retrieved on Jul. 20, 2004]. Retrieved from the internet: GenBank Accession No. AAH22021.

Hashimoto, K., et al., "Hypothetical protein [Macaca fascicularis]", Aug. 16, 2001 (sequence) GenBank [online] Bethesda, MD, USA: National Center for Biotechnology Information [retrieved on Jul. 20, 2004]. Retrieved from the internet: GenBank Accession No. BAB62998.

Hashimoto, K., et al., "Hypothetical protein [Macaca fascicularis]", Feb. 22, 2003 (sequence) GenBank [online] Bethesda, MD, USA: National Center for Biotechnology Information [retrieved on Jul. 20, 2004]. Retrieved from the internet: GenBank Accession No. BAB62965.

Guo, J. H., et al., "unknown [*Homo Sapiens*]", May 01, 2002 (sequence) Genbank [online] Bethesda, MD, USA: National Center for Biotechnology Information [retrieved on Jul. 20, 2004]. Retrieved from the internet: GenBank Accession No. AAM20912.

Hashimoto, K., et al., "Hypothetical protein [Macaca fascicularis]", Aug. 16, 2001 (sequence) GenBank [online] Bethesda, MD, USA: National Center for Biotechnology Information [retrieved on Jul. 20, 2004]. Retrieved from the internet: GenBank Accession No. BAB62930.

Guo, J. H., et al., "unknown [*Homo Sapiens*]", Jul. 23, 2003 (sequence) Genbank [online] Bethesda, MD, USA: National Center for Biotechnology Information [retrieved on Jul. 20, 2004]. Retrieved from the internet: GenBank Accession No. AAP97318.

* cited by examiner

```
AGCGGAGCTCAACCAGGTATCTGCTTGGAACCCAGCCACCATAAAGCCTGCTAGCTAAAAAAAAWTTTTACATCTCTCA    SEQ ID NO:1
GTTCATTCGGCACAGACCCCTGCCTCATTCACCTGTGACTCTGCTTGGAAAATTCATCAGTTACAAAGCAGCCAATGCA
ATTATCTCAAGGCATTGAATTCTGCATCTTTTAGTGAAGAAAATAACTGAACATGGTTTTCTTCTGAAGACACAAGTC
CAAAGGCCAATCACACACCTCTTACATCGATCTCTTGGAAATTGAAAAATGGACCTTTGAAAATGCTAGATTTACA
```

```
          M   R   N   A   I   I   Q   G   L   F   Y   G   S   L   T   F   G   I   W   T    20   SEQ ID NO:2
         ATG AGA AAT GCC ATA ATT CAA GGT TTA TTC TAT GGG TCC TTG ACA TTT GGG ATC TGG ACA   60
↑SEQ ID NO:3→
          A   L   L   F   I   Y   L   H   H   N   H   V   S   S   W   Q   K   K   S   Q    40
         GCT CTG TTA TTC ATA TAT TTG CAC CAT AAT CAT GTG AGC AGC TGG CAG AAG AAA AGC CAG  120

E   P   L   S   A   W   S   P   G   K   K   V   H   Q   Q   I   I   Y   G   S    60
         GAG CCT CTG TCA GCT TGG TCC CCT GGA AAA AAA GTG CAT CAG CAA ATT ATC TAT GGC TCA  180

E   Q   I   P   K   P   H   V   I   V   K   R   T   D   E   D   K   A   K   S    80
         GAG CAA ATA CCA AAA CCT CAT GTA ATA GTC AAA AGG ACT GAT GAA GAT AAA GCA AAG TCT  240

M   L   G   T   D   F   N   H   T   N   P   E   L   H   K   E   L   L   K   Y   100
         ATG TTA GGT ACA GAT TTT AAC CAT ACA AAC CCA GAA CTT CAT AAA GAA CTT TTA AAA TAT  300

G   F   N   V   I   I   S   R   S   L   G   I   E   R   E   V   P   D   T   R   120
         GGA TTT AAT GTG ATT ATC AGT AGA AGC TTG GGC ATC GAA AGA GAA GTG CCA GAT ACC AGG  360

S   K   M   R   L   Q   K   H   Y   P   A   R   L   P   T   A   S   I   V   I   140
         AGT AAA ATG CGT CTT CAA AAA CAT TAC CCA GCC CGC CTC CCG ACT GCC AGC ATT GTC ATT  420

C   F   Y   N   E   E   C   N   A   L   F   Q   T   M   S   S   V   T   N   L   160
         TGC TTC TAT AAT GAA GAA TGT AAT GCC TTG TTT CAG ACC ATG TCC AGT GTC ACG AAC CTC  480

T   P   H   Y   F   L   E   E   I   I   L   V   D   D   M   S   K   V   D   D   180
         ACG CCA CAC TAT TTT CTT GAA GAA ATT ATT TTG GTA GAT GAC ATG AGC AAA GTT GAT GAT  540

L   K   E   K   L   D   Y   H   L   E   T   F   R   G   K   V   K   I   I   R   200
         TTG AAA GAA AAA CTA GAC TAT CAC CTG GAA ACT TTT CGG GGA AAG GTT AAA ATA ATA AGA  600

N   K   K   R   E   G   L   I   R   A   R   L   I   G   A   S   H   A   S   G   220
         AAC AAA AAG AGA GAG GGG CTG ATT CGA GCA AGG CTG ATT GGA GCT TCT CAT GCT TCA GGG  660

D   V   L   V   F   L   D   S   H   C   E   V   N   R   V   W   L   E   P   L   240
         GAT GTT CTG GTG TTC CTG GAC AGC CAC TGT GAG GTG AAC AGA GTA TGG CTG GAG CCC CTG  720

L   H   A   I   A   K   D   P   K   M   V   V   C   P   L   I   D   V   I   D   260
         CTG CAT GCC ATT GCC AAG GAC CCC AAA ATG GTG GTG TGC CCC CTG ATA GAT GTC ATT GAT  780

D   R   T   L   E   Y   K   P   S   P   L   V   R   G   T   F   D   W   N   L   280
         GAT AGA ACT CTG GAG TAT AAG CCC TCT CCT CTT GTA AGG GGA ACT TTT GAT TGG AAC CTA  840

Q   F   K   W   D   N   V   F   S   Y   E   M   D   G   P   E   G   S   T   K   300
         CAA TTT AAA TGG GAT AAT GTT TTC TCT TAT GAG ATG GAT GGA CCA GAA GGA TCT ACT AAA  900

P   I   R   S   P   A   M   S   G   G   I   F   A   I   R   R   H   Y   F   N   320
         CCA ATC CGG TCA CCT GCA ATG TCT GGA GGA ATT TTT GCT ATA CGT CGG CAT TAT TTT AAT  960

E   I   G   Q   Y   D   K   D   M   D   F   W   G   R   E   N   L   E   L   S   340
         GAA ATT GGA CAG TAT GAC AAG GAT ATG GAT TTT TGG GGA AGA GAA AAT TTG GAA CTT TCA 1020

L   R   I   W   M   C   G   G   Q   L   F   I   I   P   C   S   R   V   G   H   360
         CTA AGG ATC TGG ATG TGT GGA GGC CAA CTC TTT ATA ATC CCC TGC TCT CGA GTA GGA CAT 1080

I   S   K   K   Q   T   G   K   P   S   T   I   I   S   A   M   T   H   N   Y   380
         ATC AGT AAG AAA CAA ACT GGA AAA CCT TCT ACA ATC ATC AGT GCT ATG ACA CAT AAC TAC 1140

L   R   L   V   H   V   W   L   D   E   Y   K   E   Q   F   F   L   R   K   P   400
         CTA AGA CTG GTG CAC GTT TGG CTG GAT GAA TAT AAG CAG CAG TTT TTT CTT CGA AAG CCT 1200
```

FIGURE 1a

```
    G   L   K   Y   V   T   Y   G   N   I   R   E   R   V   E   L   R   K   R   L    420
   GGT CTG AAA TAT GTC ACC TAC GGA AAT ATT CGC GAG CGT GTT GAG TTA AGG AAA CGA CTG   1260

G   C   K   S   F   Q   W   Y   L   D   N   V   F   P   E   L   E   A   S   V    440
   GGT TGC AAG TCA TTT CAG TGG TAT TTG GAT AAT GTC TTC CCA GAG TTG GAG GCA TCT GTG   1320

N   S   L   *                                                                     444
   AAC AGC CTG TGA                                                                   1332
       ←SEQ ID NO:3↑
   AAGGAAAACAAATCACTTTCATTAATAAAGGGTTAAAAGTCTCCTAGTCATTCAACATAGTGTCACAAGAGTGTAAGTT

TGGAACATCGTGGAATTACGTGAAATGCAATTAAAAAAATATGACCAGAAAAAAAAAAAAAAA
```

FIGURE 1b

```
                *->SiiiPtYNe.ekyleecleSllnQt.tyenfEiivVDDgS.tDgtve
                 Si+i++YNe+ + l ++  S+ n t+ y   Eii+VDD S+ D+++e
47153     137   SIVICFYNEeCNALFQTMSSVTNLTpHYFLEEIILVDDMSkVDDLKE  183 ileeyak..dprirvirleenlGlaaArNaGlkhAtGdydyiaflDaDde
                l+ + ++  ++++ir+++++Gl++Ar +G++hA+Gd  +++flD+++e
47153     184   KLDYHLEtfRGKVKIIRNKKREGLIRARLIGASHASGD--VLVFLDSHCE  231 v.pdwlekllellekngadivig.rv.in.e.n.kgr............
                v+  wle+ll ++ k+++ +v++ ++ i++ +  ++++++  +++ + +
47153     232   VnRVWLEPLLHAIAKDPKMVVCPlIDvIDdRtLeYKPsplvrgtfdwnlq  281

.........lngk.l.r.l.l.v.fligsnalyrrealekll<-*    SEQ ID NO:4
                + ++ +     +++ +++++ + ++g+ +++rr   +++++
47153     282   fkwdnvfsyEMDGpEgStKpIrSpAMSGGIFAIRRHYFNEIG          323
```

FIGURE 3

```
Query:   299 TKPIRSPAMSGGIFAIRRHYFNEIGQYDKDMDFWGRENLELSLRIWMCGGQLFIIPCSRV 358
             T PIRSP M+GG+FAI + YF E+G YD  MD WG ENLELS R+W CGG+L I+PCS V
Sbjct:    18 TDPIRSPTMAGGLFAINKEYFEELGTYDPGMDIWGGENLELSFRVWQCGGRLEIVPCSHV  77

Query:   359 GHISKKQT-----GKPSTIISAMTHNYLRLVHVWLDEYKEQFFLRKPGLKYVT-YGNIRE 412
             GH+ +K++     GK S    ++ N +R+  VW+D+YKE F+   P  + V  +G+I E
Sbjct:    78 GHVFRKRSPYTFPGKGSGK-DVISRNTVRVAEVWMDDYKEYFYKHNPQARKVRDFGDISE 136

Query:   413 RVELRKRLGCKSFQWYLDNVFPEL 436
             R ELR++L CKSF+WYL+NV P+L
Sbjct:   137 RKELREKLQCKSFKWYLENVYPDL 160  SEQ ID NO:5
```

FIGURE 4

```
Query:   135 TASIVICFYNEECNALFQTMSSVTN--LTPHYFLEEIILVDDMS--KVDDLKEKLDYHLE 190
             + S++I  YNEE + L   +SSV      HY +EEII+VDD S     ++ E+  Y  E
Sbjct:     1 SVSVIIPTYNEEESILKTLVSSVLQQQYENHYEMEEIIIVDDGSTDNTAEIVEEYSYSAE 60

Query:   191 T-FRGKVKIIRNKKREGLIRARLIGASHA-SG------DVLVFLDSH-CEVNRVWLEPLL 241
               R KVK+IRN+K  G+   A   G HA SG      D +VFLDS    ++ WLE L+
Sbjct:    61 KESRVKVKVIRNEKNSGMSSAMNKGLKHALSGADGDIIDYIVFLDSDDVHMSPDWLEKLI 120

Query:   242 HAIAKDPKMVVCPLIDVIDDRTLEYKPSP-LVR--GTFDWNLQF 282
              A+ +D  VV    V++D +Y + L+   G ++W++ +
Sbjct:   121 EAMEEDNADVVVGSRQVVNDDNKQYSSATRLINMEGGYNWSMMY 164  SEQ ID NO:6
```

FIGURE 5

```
Query:   99  KYGFNVIISRSLGIEREVPDTRS-KMRLQKHYPARLPTASIVICFYNEECNALFQTMSSV 157
             KY FN +S  + + R +PDTR  + +  +K+Y    LPT S++I F+NE + L +T+ SV
Sbjct:   15  KYAFNAYVSDRISLNRSIPDTRHPECKNKKYYSDNLPTTSVIIVFHNEAWSTLLRTVHSV 74

Query:  158  TNLTPHYFLEEIILVDDMS-KVDDLKEKLD-YHLETFRGKVKIIRNKKREGLIRAR 211
             N TP + L+EIILVDD S +    LK+KL+ Y  + F GKVKI+RN++REGLIRAR
Sbjct:   75  INRTPPHLLKEIILVDDFSDRPHLLKQKLEEYVKKKFPGKVKILRNEEREGLIRAR 130   SEQ ID NO:7
```

FIGURE 6

```
Query:  255  LIDVIDDRTLEY---KPSPLVRGTFDWNLQFKWDNVFSYEMDGP---EGSTKPIRSPAMS 308
             +IDVIDD T EY   K S   RG FDW L FKW +   E       E T+PIRSP M+
Sbjct:    1  VIDVIDDNTFEYHKSKSSDTSRGGFDWGLHFKWHPIPEEERKRKKRREDPTEPIRSPTMA 60

Query:  309  GGIFAIRRHYFNEIGQYD 326
             GG+FAI R YF E+G YD
Sbjct:   61  GGLFAIDREYFWELGSYD 78   SEQ ID NO:8
```

FIGURE 7

```
Query:  329  MDFWGRENLELSLRIWMCGGQLFIIPCSRVGHISKKQT------GKPSTIISAMTHNYLR 382
             MD WG ENLELS R+W CGG+L I+PCSRVGHI +KQ+      G   S +IS   NY R
Sbjct:    1  MDIWGGENLELSFRVWQCGGKLEIVPCSRVGHIFRKQSPYTFPSGSSSNVIS---RNYKR 57

Query:  383  LVHVW 387
             +  VW
Sbjct:   58  VAEVW 62   SEQ ID NO:9
```

FIGURE 8

```
Query:  388  LDEYKEQFFLRKPGL-KYVTYGNIRERVELRKRLGCKSFQWYLDNVFPEL 436
             +DEYKE F+ R+P   + V YG+I ER+ELR++L CKSF+WYL+NV PEL
Sbjct:    1  MDEYKEYFYKRRPNAYRNVDYGDISERMELREKLQCKSFKWYLENVYPEL 50   SEQ ID NO:10
```

FIGURE 9

```
Query:  212 LIGASHASGDVLVFLDSHCEVNRVWLEPLLHAIAKDPKMVVCP 254
            LIGA  A+G+VL FLDSHCE N  WLEPLL  I +D    VVCP
Sbjct:    1 LIGAKVATGEVLTFLDSHCECNEGWLEPLLERIKEDRTTVVCP  43    SEQ ID NO:11
```

FIGURE 10

```
Query:  307 MSGGIFAIRRHYFNEIGQYDKDMDFWGRENLELSLRIWMCGGQLFIIPCSRVGHISKKQ 365
            +SG  FA+R+  F ++G +D+ M  +G E + L  +I   G    I+  S +G++  K+
Sbjct:  167 ISGACFAVRKSVFTKVGMFDEQMFLYGEERM-LHYKILRLGNY-HIVYDSTIGYLHPKE 223   SEQ ID
NO:12
```

FIGURE 11a

```
Query:  137 SIVICFYNEECNALFQTMSSVTNLTPHYFLEEIILVDDMSKVDDLKEKLDYHLETFRGKV 196
            S+VI  +N EN +    + S+          E++LVD+ SK +         E + KV
Sbjct:   11 SVVIVTFNSE-NLIMDCLDSIFKYNDISDDLEVVLVDNCSK--NYLSMFGSIEEKYGNKV  67

Query:  197 KIIRNKKREGLIRARLIGASHASGDVLVFLD 227
            +I NK   G  +  +G A   +++ ++
Sbjct:   68 VLINNKVNGGYGQGNNLGVEVAKAPIILIMN  98    SEQ ID NO:13
```

FIGURE 11b

```
Query:  325 YDKDMDFWG-RENLELSLRIWMCGGQLFIIPCSRVG 359
            YD  +  +  +EN E S +  ++ G    FI  C ++G
Sbjct:  212 YDSTIGYLHPKENREFSSKNFLLGYHSFIYTCDKLG 247   SEQ ID NO:14
```

FIGURE 11c

47153, A HUMAN GLYCOSYLTRANSFERASE FAMILY MEMBER AND USES THEREFOR

This application claims priority on U.S. Application Ser. No. 60/279,647 filed 28 Mar. 2001, which is relied on and incorporated herein by reference in its entirety.

BACKGROUND OF THE INVENTION

Transferases catalyze the transfer of one molecular group from one molecule to another. Such molecular groups include phosphate, amino, methyl, formyl, acetyl, acyl, glycosyl, phosphatidyl, phosphoribosyl, among other groups.

One such type of transferase is glycosyltransferase. A great diversity of oligosaccharide structures and types of glycoconjugates is found in nature, and these are synthesized by a large number of glycosyltransferases. Glycosyltransferases catalyze the synthesis of glycoconjugates, including glycolipids, glycoproteins, and polysaccharides, by transferring an activated mono- or oligosaccharide residue to an existing acceptor molecule for the initiation or elongation of the carbohydrate chain. A catalytic reaction is believed to involve the recognition of both the donor and acceptor by suitable domains, as well as the catalytic site of the enzyme (Amado et al. (1999) *Biochim Biophys Acta* 1473:35–53; Kapitonov et al. (1999) Glycobiology 9:961–78).

Because the glycosylation reaction is highly specific with respect to both the configuration of the sugar residue and the site of the addition, it is expected that unique domain structures for substrate recognition and nucleotide-sugar binding are located within the enzyme molecule. Evidence indicates that formation of many glycosidic linkages is covered by large homologous glycosyltransferase gene families, and that the existence of multiple enzyme isoforms provides a degree of redundancy as well as a higher level of regulation of the glycoforms synthesized (Kapitonov et al. (1999) Glycobiology 9:961–78).

Glycosylation is the principal chemical modification to proteins as they pass through Golgi vesicles. Glycosyltransferases of the Golgi do not possess an obvious sequence homology which would suggest a common Golgi retention signal. However, they are all membrane proteins and share type II topology, consisting of an amino terminal cytoplasmic tail, a signal anchor transmembrane domain, a stem region, and a large luminal catalytic domain. The membrane-spanning domain and its flanking regions contain necessary and sufficient information for Golgi retention of these enzymes (Jaskiewicz (1997) Acta Biochim Pol 44:173–9). ER localized glycosyltransferases can have either a type II topology, like the Golgi glycosyltransferases, or a type I topology, e.g., the N-terminus and catalytic domain inside the ER (Kapitonov et al. (1999) Glycobiology 9:961–78). Some glycosyltransferases are present on the cell surface and are thought to function as cell adhesion molecules by binding oligosaccharide substrates on adjacent cell surfaces or in the extracellular matrix. The best studied of these is beta 1,4-galactosyltransferase, which mediates sperm binding to the egg coat and selected cell interactions with the basal lamina (Shur (1993) Curr Opin Cell Biol 5:854–63).

Mucin type O-glycosidically linked oligosaccharides have been described on a wide variety of protein molecules (Sadler, 1984). These structures constitute essential components in an equally wide variety of biological functions (e.g., Paulson, 1989; Jentoft, 1990 and references therein). The initial reaction in the biosynthesis of O-linked oligosaccharides is the transfer of N-acetylgalactosamine from the nucleotide sugar, UDP-N-acetylgalactosmine, to a serine or threonine residue on the acceptor polypeptide. This reaction, which can occur post-translationally, is catalyzed by a GalNAc-transferase enzyme (GalNAcT) called, UDP-GalNAc:polypeptide, N-acetylgalactosaminyltransferase. This is an intracellular membrane bound enzyme believed to be localized in the secretory pathway.

SUMMARY OF THE INVENTION

The present invention is based, in part, on the discovery of a novel glycosyltransferase family member, referred to herein as "47153". The nucleotide sequence of a cDNA encoding 47153 is shown in SEQ ID NO:1, and the amino acid sequence of a 47153 polypeptide is shown in SEQ ID NO:2. In addition, the nucleotide sequence of the coding region is depicted in SEQ ID NO:3.

Accordingly, in one aspect, the invention features a nucleic acid molecule which encodes a 47153 protein or polypeptide, e.g., a biologically active portion of the 47153 protein. In a preferred embodiment, the isolated nucleic acid molecule encodes a polypeptide having the amino acid sequence of SEQ ID NO:2. In other embodiments, the invention provides isolated 47153 nucleic acid molecules having the nucleotide sequence shown in SEQ ID NO:1 or SEQ ID NO:3. In still other embodiments, the invention provides nucleic acid molecules that are sufficiently or substantially identical (e.g., naturally occurring allelic variants) to the nucleotide sequence shown in SEQ ID NO:1 or SEQ ID NO:3. In other embodiments, the invention provides a nucleic acid molecule which hybridizes under stringent hybridization conditions to a nucleic acid molecule comprising the nucleotide sequence of SEQ ID NO:1 or SEQ ID NO:3, wherein the nucleic acid encodes a full length 47153 protein or an active fragment thereof.

In a related aspect, the invention further provides nucleic acid constructs which include a 47153 nucleic acid molecule described herein. In certain embodiments, the nucleic acid molecules of the invention are operatively linked to native or heterologous regulatory sequences. Also included are vectors and host cells containing the 47153 nucleic acid molecules of the invention e.g., vectors and host cells suitable for producing polypeptides.

In another related aspect, the invention provides nucleic acid fragments suitable as primers or hybridization probes for the detection of 47153-encoding nucleic acids.

In still another related aspect, isolated nucleic acid molecules that are antisense to a 47153 encoding nucleic acid molecule are provided.

In another aspect, the invention features 47153 polypeptides, and biologically active or antigenic fragments thereof that are useful, e.g., as reagents or targets in assays applicable to treatment and diagnosis of glycosyltransferase-associated or other 47153-associated disorders. In another embodiment, the invention provides 47153 polypeptides having a 47153 activity. Preferred polypeptides are 47153 proteins including at least one glycosyltransferase domain, and, preferably, having a 47153 activity, e.g., a 47153 activity as described herein. In a further preferred embodiment, the 47153 molecules of the invention are useful in treating brain disorders.

In other embodiments, the invention provides 47153 polypeptides, e.g., a 47153 polypeptide having the amino acid sequence shown in SEQ ID NO:2; an amino acid sequence that is sufficiently or substantially identical to the amino acid sequence shown in SEQ ID NO:2; or an amino acid sequence encoded by a nucleic acid molecule having a nucleotide sequence which hybridizes under stringent hybridization conditions to a nucleic acid molecule comprising the nucleotide sequence of SEQ ID NO:1 or SEQ ID NO:3, wherein the nucleic acid encodes a full length 47153 protein or an active fragment thereof.

In a related aspect, the invention further provides nucleic acid constructs which include a 47153 nucleic acid molecule described herein.

In a related aspect, the invention provides 47153 polypeptides or fragments operatively linked to non-47153 polypeptides to form fusion proteins.

In another aspect, the invention features antibodies and antigen-binding fragments thereof, that react with, or more preferably specifically or selectively bind 47153 polypeptides.

In another aspect, the invention provides methods of screening for compounds that modulate the expression or activity of the 47153 polypeptides or nucleic acids.

In still another aspect, the invention provides a process for modulating 47153 polypeptide or nucleic acid expression or activity, e.g., using the compounds identified in the screens described herein. In certain embodiments, the methods involve treatment of conditions related to aberrant activity or expression of the 47153 polypeptides or nucleic acids, such as conditions involving aberrant or deficient glycosyltransferase function. Examples of such disorders, e.g., glycosyltransferase-associated or other 47153-associated disorders, include but are not limited to, cellular proliferative and/or differentiative disorders, disorders associated with bone metabolism, immune e.g., inflammatory disorders, cardiovascular disorders, including endothelial cell disorders, liver disorders, viral diseases, pain or metabolic disorders.

The invention also provides assays for determining the activity of or the presence or absence of 47153 polypeptides or nucleic acid molecules in a biological sample, including for disease diagnosis.

In a further aspect, the invention provides assays for determining the presence or absence of a genetic alteration in a 47153 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 47153 molecule. In one embodiment, the capture probe is a nucleic acid, e.g., a probe complementary to a 47153 nucleic acid sequence. In another embodiment, the capture probe is a polypeptide, e.g., an antibody specific for 47153 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIG. 1 depicts a cDNA sequence (SEQ ID NO:1) and predicted amino acid sequence (SEQ ID NO:2) of human 47153. The methionine-initiated open reading frame of human 47153 (without the 5' and 3' untranslated regions of SEQ ID NO:1) is shown also as the coding sequence, SEQ ID NO:3.

FIG. 3 depicts an alignment of the glycosyltransferase domain of human 47153 with a consensus amino acid sequence derived from a hidden Markov model (HMM) from PFAM. The upper sequence is the consensus amino acid sequence (SEQ ID NO:4), while the lower amino acid sequence corresponds to amino acids 137 to 323 of SEQ. ID NO:2.

FIG. 4 depicts a BLAST alignment of human 47153 with a consensus amino acid sequence derived from a ProDomain No. PD003162 ("N-acetylgalactosaminyltransferase polypeptide acetylgalactosaminyltransferase UDP-GALNAC: polypeptide glycosyltransferase protein-UDP protein" (Release 1999.2; see also ProDom family PD003162, ProDomain Release 2001.3; www.toulouse.inra.fr/prodom.html). The lower sequence is amino acid residues 18 to 160 of the 172 amino acid consensus sequence (SEQ ID NO:5), while the upper amino acid sequence corresponds to the N-acetylgalactosaminyltransferase domain of human 47153, amino acid residues 299 to 436 of SEQ ID NO:2.

FIG. 5 depicts a BLAST alignment of human 47153 with a consensus amino acid sequence derived from a ProDomain No. PD000196 ("protein transferase glycosyltransferase putative biosynthesis glycosyl synthase transmembrane N-acetylgalactosaminyltransferase membrane" (Release 1999.2; see also ProDom family PD003162, ProDomain Release 2000.1; www.toulouse.inra.fr/prodom.html). The lower sequence is amino acid residues 1 to 164 of the 196 amino acid consensus sequence (SEQ ID NO:6), while the upper amino acid sequence corresponds to the N-acetylgalactosaminyltransferase domain of human 47153, amino acid residues 135 to 282 of SEQ ID NO:2.

FIG. 6 depicts a BLAST alignment of human 47153 with a consensus amino acid sequence derived from a ProDomain No. PD003677 ("acetylgalactosaminyltransferase N-acetylgalactosaminyltransferase polypeptide UDP-GALNAC: polypeptide protein-glyco glycosyltransferase" (Release 2001.1; www.toulouse.inra.fr/prodom.html). The lower sequence is amino acid residues 15 to 130 of the 130 amino acid consensus sequence (SEQ ID NO:7), while the upper amino acid sequence corresponds to the N-acetylgalactosaminyltransferase domain of human 47153, amino acid residues 99 to 211 of SEQ ID NO:2.

FIG. 7 depicts a BLAST alignment of human 47153 with a consensus amino acid sequence derived from a ProDomain No. PD001297 ("N-acetylgalactosaminyltransferase polypeptide UDP-GALNAC: polypeptide protein-glyco glycosyltransferase" (Release Release 2001.1; www.toulouse.inra.fr/prodom.html). The lower sequence is amino acid residues 1 to 78 of the 80 amino acid consensus sequence (SEQ ID NO:8), while the upper amino acid sequence corresponds to the N-acetylgalactosaminyltransferase domain of human 47153, amino acid residues 255 to 326 of SEQ ID NO:2.

FIG. 8 depicts a BLAST alignment of human 47153 with a consensus amino acid sequence derived from a ProDomain No. PD003162 ("acetylgalactosaminyltransferase N-acetylgalactosaminyltransferase polypeptide UDP-GALNAC: polypeptide protein—FIS GALNAC-TI" (Release 2001.1; www.toulouse.inra.fr/prodom.html). The lower sequence is amino acid residues 1 to 62 of the 62 amino acid consensus sequence (SEQ ID NO:9), while the upper amino acid sequence corresponds to the N-acetylgalactosaminyltransferase domain of human 47153, amino acid residues 329 to 387 of SEQ ID NO:2.

FIG. 9 depicts a BLAST alignment of human 47153 with a consensus amino acid sequence derived from a ProDomain No. PD092750 ("acetylgalactosaminyltransferase N-acetylgalactosaminyltransferase polypeptide UDP-GALNAC: polypeptide protein—FIS GALNAC-TI" (Release 2001.1; www.toulouse.inra.fr/prodom.html). The lower sequence is amino acid residues 1 to 50 of the 72 amino acid consensus sequence (SEQ ID NO:10), while the upper amino acid sequence corresponds to the N-acetylgalactosaminyltransferase domain of human 47153, amino acid residues 388 to 436 of SEQ ID NO:2.

FIG. 10 depicts a BLAST alignment of human 47153 with a consensus amino acid sequence derived from a ProDomain No. PD003005 ("acetylgalactosaminyltransferase N-acetylgalactosaminyltransferase polypeptide UDP-GALNAC: polypeptide protein-glyco GALNAC-TI" (Release 2001.1; www.toulouse.inra.fr/prodom.html). The lower sequence is amino acid residues 1 to 43 of the 43 amino acid consensus sequence (SEQ ID NO:11), while the upper amino acid sequence corresponds to the N-acetylgalactosaminyltransferase domain of human 47153, amino acid residues 212 to 254 of SEQ ID NO:2.

FIGS. 11a–c depict a BLAST alignment of human 47153 with a consensus amino acid sequence derived from a ProDomain No. PD318117 ("transferase glycosyl" (Release 2001.1; www.toulouse.inra.fr/prodom.html). The lower sequence is amino acid residues 167–223, 11–98, and 212–247 of the 291 amino acid consensus sequence (SEQ ID NOs:12, 13, and 14), while the upper amino acid sequence corresponds to the N-acetylgalactosaminyltransferase domain of human 47153, amino acid residues 388 to 436 of SEQ ID NO:2. The BLAST algorithm identifies multiple local alignments between the consensus amino acid sequence and human 47153. FIG. 11a depicts the first local alignment, FIG. 11b the second, and FIG. 11c the third.

DETAILED DESCRIPTION OF THE INVENTION

Figure 2:
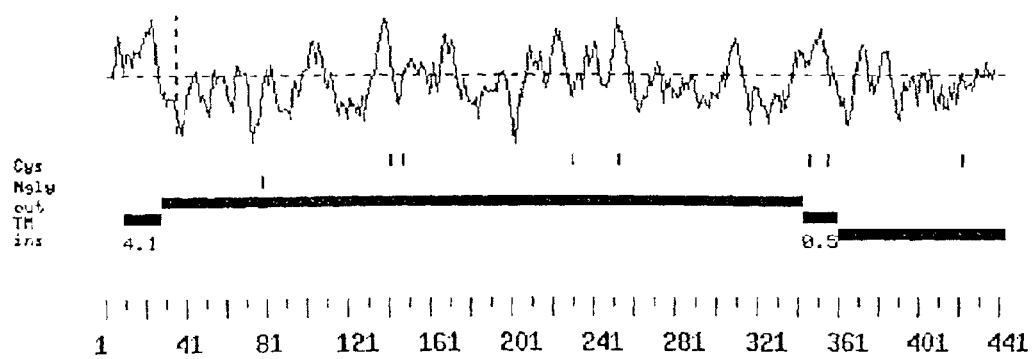
FIG. 2 depicts a hydropathy plot of human 47153. Relatively hydrophobic residues are shown above the dashed horizontal line, and relatively hydrophilic residues are below the dashed horizontal line. The cysteine residues (cys) and N-glycosylation sites (Ngly) are indicated by short vertical lines just below the hydropathy trace. The numbers corresponding to the amino acid sequence of human 47153 are indicated. Polypeptides of the invention include fragments which include; all or part of a hydrophobic sequence, e.g., a sequence above the dashed line, e.g., the sequence from about amino acid 100 to 110, from about 250 to 260, and from about 340 to 360 of SEQ ID NO:2; all or part of a hydrophilic sequence, e.g., a sequence below the dashed line, e.g., the sequence from about amino acid 85 to 100, from about 180 to 200, and from about 280 to 300 of SEQ ID NO:2; a sequence which includes a Cys, or a glycosylation site.

The human 47153 sequence (FIG. 1; SEQ ID NO:1), which is approximately 1788 nucleotides long including untranslated regions, contains a predicted methionine-initiated coding sequence of about 1332 nucleotides, including the termination codon (nucleotides indicated as coding of SEQ ID NO:1 in FIG. 1; SEQ ID NO:3). The coding sequence encodes a 443 amino acid protein (SEQ ID NO:2).

The human 47153 protein of SEQ ID NO:2 and FIG. 2 includes an amino-terminal hydrophobic amino acid sequence, consistent with a signal sequence, of about 34 amino acids (from amino acid 1 to about amino acid 34 of SEQ ID NO:2, PSORT, Nakai, K. and Kanehisa, M. (1992) *Genomics* 14:897–911), which upon cleavage results in the production of a mature protein form. This mature protein form is approximately 409 amino acid residues in length (from about amino acid 35 to amino acid 443 of SEQ ID NO:2).

Human 47153 contains the following regions or other structural features (for general information regarding PFAM identifiers, PS prefix and PF prefix domain identification numbers, refer to Sonnhammer et al. (1997) *Protein* 28:405–420 and www.psc.edu/general/software/packges/pfam/pfam.html):

a glycosyltransferase domain (PFAM Accession Number PF00535) located at about amino acid residues 137 to 323 of SEQ ID NO:2;

two transmembrane domains (predicted by MEMSAT, Jones et al. (1994) *Biochemistry* 33:3038–3049) at about amino acids 9 to 27 and 343 to 359 of SEQ ID NO:2;

one N-glycosylation site (Prosite PS00001) from about amino acids 87 to 90 of SEQ ID NO:2;

one cAMP/cGMP-dependent protein kinase phosphorylation sites (Prosite PS00004) located at about amino acids 363 to 366 of SEQ ID NO:2;

five protein kinase C phosphorylation sites (Prosite PS00005) at about amino acids 191 to 193, 298 to 300, 340 to 342, 362 to 364, and 366 to 368 of SEQ ID NO:2;

four casein kinase II phosphorylation sites (Prosite PS00006) located at about amino acids 73 to 76, 89 to 92, 176 to 179, and 228 to 231 of SEQ ID NO:2;

six N-myristoylation sites (Prosite PS00008) from about amino acids 8 to 13, 17 to 22, 83 to 88, 206 to 211, 214 to 219, and 309 to 314 of SEQ ID NO:2;

one amidation site (Prosite PS00009) from about amino acids 48 to 51 of SEQ ID NO:2; and one second peroxisomal targeting signal (as predicted by PSORT) from about amino acids 342 to 350 of SEQ ID NO:2.

The 47153 protein contains a significant number of structural characteristics in common with members of the glycosyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologs of non-human origin, e.g., rat or mouse proteins. Members of a family also can have common functional characteristics.

As used herein, the term "glycosyltransferase" includes a protein or polypeptide which is capable of catalyzing the synthesis of glycoconjugates, including glycolipids, glycoproteins, and polysaccharides, by transferring an activated mono- or oligosaccharide residue to an existing acceptor molecule for the initiation or elongation of the carbohydrate chain. The acceptor can be a lipid, a protein, a heterocyclic compound, or another carbohydrate residue.

Glycosyltransferases can be divided into numerous subfamilies based upon their specificity for sugar moieties and acceptor molecules. The glycosyltransferase domain of human 47153 bears similarity to a subfamily designated "group 2" glycosyltransferases. These enzymes comprise a diverse subfamily, whose members transfer sugar from UDP-glucose, UDP-N-acetyl-galactosamine, GDP-mannose or CDP-abequose, to a range of substrates including cellulose, dolichol phosphate and teichoic acids. Based on the sequence similarities, the 47153 molecules of the present invention are predicted to have similar biological activities as glycosyltransferase family members.

Glycosyltransferases play roles in diverse cellular processes. For example, the major target of the natural IgM and IgG antibodies during hyperacute xenograft rejection is the terminal carbohydrate epitope Gal alpha(1,3)Gal, formed by the alpha 1,3galactosyl transferase, which places a terminal galactose residue in an alpha-linkage to another galactose (Sandrin et al. (1994) *Immunol Rev* 141:169–90). As another example, mutations in the Piga gene, the protein product of which mediates N-acetylglucosamine attachment to phosphatidylinositol, results in the clonal hematologic disorder, paroxysmal nocturnal hemoglobinuria (Ware et al. (1994) Blood 83:2418–22). Additionally, UDP-galactose:ceramide galactosyltransferase is the enzyme responsible for the biosynthesis of galactosylceramide, a molecule thought to play a critical role in myelin formation, signal transduction, viral and microbial adhesion, and oligodendrocyte development (Kapitonov et al. (1999) Glycobiology 9:961–78).

Glycosylation of glycoproteins and glycolipids is one of many molecular changes that accompany malignant transformation. GlcNAc-branched N-glycans and terminal Lewis antigen sequences have been observed to increase in some cancers, and to correlate with poor prognosis (Dennis et al. (1999) Biochim Biophys Acta 1473:21–34). Cellular membrane over-expression and shedding of acidic glycosphingolipids into the interstitial spaces and blood of cancer patients may play a central role in increased tumor cell growth, lack of immune cell recognition and neovascularization and could represent a molecular target for cancer therapy (Fish (1996) Med Hypotheses 46:140–44). Thus, the 47153 molecules of the present invention may be involved in:

1) the transfer of an activated sugar residue to an acceptor molecule; 2) the processing, folding, and secretion of proteins; 3) the modulation of tumor cell growth and invasion; 4) myelin formation; 5) signal transduction; 6) viral and microbial adhesion; 7) oligodendrocyte development; 8) sperm-egg binding; 9) evasion of immune detection; 10) xenograft rejection; and 11) the ability to antagonize or inhibit, competitively or non-competitively, any of 1–11. Thus, the 47153 molecules can act as novel diagnostic targets and therapeutic agents for controlling glycosyltransferase-related disorders, for example, such as those diseases associated with the activities described above. As the 47153 molecules have homology to known glycosyltransferases, they are expected to be involved in controlling similar disorders.

A 47153 polypeptide can include a "glycosyltransferase domain" or regions homologous with a "glycosyltransferase domain".

As used herein, the term "glycosyltransferase domain" includes an amino acid sequence of about 150 to 200 amino acid residues in length and having a bit score for the alignment of the sequence to the glycosyltransferase domain (HMM) of at least 50. Preferably a glycosyltransferase domain mediates the catalysis of glycoconjugate synthesis. Preferably, a glycosyltransferase domain includes at least about 155 to 185 amino acids, more preferably about 165 to 190 amino acid residues, or about 185 to 190 amino acids and has a bit score for the alignment of the sequence to the glycosyltransferase domain (HMM) of at least 50, 90, 110 or greater. The glycosyltransferase domain (HMM) has been assigned the PFAM Accession Number PF00535 genome.wustl.edu/Pfam.html). An alignment of the glycosyltransferase domain (amino acids 137 to 323 of SEQ ID NO:2) of human 47153 with a consensus amino acid sequence (SEQ ID NO:4) derived from a hidden Markov model is depicted in FIG. 3.

The glycosyltransferase domain is homologous to ProDom families PD003162, PD000196, PD003677, PD001297, PD092750, PD003005 and PD318117 ("N-acetylgalactosaminyltransferase", SEQ ID NOs:5 and 7–10 and "glycosyltransferase", SEQ ID NOs:6 and 12–14, see ProDomain No. PD003162 and PD000196, ProDomain Release 2000.1; www.toulouse.inra.fr/prodom.html; see also ProDomain No. PD003162 and PD000196, Release 1999.2 and see ProDomain No. PD003162, PD092750, PD003005 and PD318117 ProDomain Release 2001.1). ProDom (derived from BLAST search) alignments of the amino acid sequence of human 47153 revealed that 47153 is similar to the N-acetylgalactosaminyltransferase protein. This amino acid molecule is approximately 52% identical to 47153, over amino acids 299–436 (SEQ ID NO:5) depicted in FIG. 4; approximately 35% identical to 47153, over amino acids 135 to 282 (SEQ ID NO:6) depicted in FIG. 5; approximately 49% identical to 47153, over amino acids 99 to 211 (SEQ ID NO:7) depicted in FIG. 6; approximately 52% identical to 47153, over amino acids 255 to 326 (SEQ ID NO:8) depicted in FIG. 7; approximately 55% identical to 47153, over amino acids 329 to 387 (SEQ ID NO:9) depicted in FIG. 8; approximately 60% identical to 47153, over amino acids 388 to 436 (SEQ ID NO:10) depicted in FIG. 9; approximately 65% identical to 47153, over amino acids 212 to 254 (SEQ ID NO:11) depicted in FIG. 10; approximately 30%, 24% and 30% identical to 47153, over amino acids 307 to 365(SEQ ID NO:12); 137 to 227 (SEQ ID NO:13) and 325 to 359 (SEQ ID NO:14) (three local alignments) respectively depicted in FIGS. 11a–c.

In a preferred embodiment, a 47153 polypeptide or protein has a "glycosyltransferase domain" or a region which includes at least about 150 to 200 more preferably about 160 to 190 or 180 to 190 amino acid residues and has at least about 60%, 70% 80% 90% 95%, 99%, or 100% homology with a "glycosyltransferase domain," e.g., the glycosyltransferase domain of human 47153 (e.g., residues 137 to 323 of SEQ ID NO:2).

To identify the presence of a "glycosyltransferase" domain in a 47153 protein sequence, and make the determination that a polypeptide or protein of interest has a particular profile, the amino acid sequence of the protein can be searched against the Pfam database of HMMs (e.g., the Pfam database, release 2.1) using the default parameters www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference. A search was performed against the HMM database resulting in the identification of a "glycosyltransferase domain" domain in the amino acid sequence of human 47153 at about residues 137 to 323 of SEQ ID NO:2 (see FIG. 1).

To identify the presence of a "glycosyltransferase" domain in a 47153 protein sequence, and make the determination that a polypeptide or protein of interest has a particular profile, the amino acid sequence of the protein can be searched against a database of domains, e.g., the ProDom database (Corpet et al. (1999), *Nucl. Acids Res.* 27:263–267). The ProDom protein domain database consists of an automatic compilation of homologous domains. Current versions of ProDom are built using recursive PSI-BLAST searches (Altschul SF et al. (1997) *Nucleic Acids Res.* 25:3389–3402; Gouzy et al. (1999) *Computers and Chemistry* 23:333–340) of the SWISS-PROT 38 and TREMBL protein databases. The database automatically generates a consensus sequence for each domain. A BLAST search was performed against the HMM database resulting in the identification of seven "glycosyltransferase" or "N-acetylgalactosaminyltransferase" domains in the amino acid sequence of human 47153 at about residues 11 to 98, 135 to 282, 167 to 223, 212 to 247, 255 to 326, 299 to 436, 329 to 387 or 388 to 436 of SEQ ID NO:2 (see FIGS. 1 and 4–11).

A 47153 polypeptide can include at least one, preferably two "transmembrane domains" or regions homologous with a "transmembrane domain". As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95% or more of the amino acids of a transmembrane domain are hydrophobic, e.g., leucines, isoleucines, tyrosines, or tryptophans. Transmembrane domains typically have alpha-helical structures and are described in, for example, Zagotta, W. N. et al., (1996) *Annual Rev. Neurosci.* 19:235–263, the contents of which are incorporated herein by reference.

In a preferred embodiment, a 47153 polypeptide or protein has at least one, preferably two "transmembrane domains" or regions which include at least about 12 to 35 more preferably about 14 to 30 or 15 to 20 amino acid residues and has at least about 60%, 70% 80% 90% 95%, 99%, or 100% homology with a "transmembrane domain," e.g., the transmembrane domains of human 47153 (e.g., residues 9 to 27 and 343 to 359 of SEQ ID NO:2). The transmembrane domain of human 47153 is visualized in the hydropathy plot (FIG. 2) as regions of about 15 to 25 amino acids where the hydropathy trace is mostly above the horizontal line.

To identify the presence of a "transmembrane" domain in a 47153 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) *Biochemistry* 33:3038–3049).

A 47153 polypeptide can include at least one, two and preferably three "non-transmembrane regions." As used herein, the term "non-transmembrane region" includes an amino acid sequence not identified as a transmembrane domain. The non-transmembrane regions in 47153 are located at about amino acids 1 to 8, 28 to 342, and 360 to 443 of SEQ ID NO:2.

The non-transmembrane regions of 47153 include at least one, preferably two cytoplasmic regions. When located at the N-terminus, the cytoplasmic region is referred to herein as the "N-terminal cytoplasmic domain." As used herein, an "N-terminal cytoplasmic domain" includes an amino acid sequence having about 1 to 15, preferably about 1 to 12, more preferably about 1 to 10, or even more preferably about 1 to 8 amino acid residues in length and is located inside of a cell or within the cytoplasm of a cell. The C-terminal amino acid residue of an "N-terminal cytoplasmic domain" is adjacent to an N-terminal amino acid residue of a transmembrane domain in a 47153 protein. For example, an N-terminal cytoplasmic domain is located at about amino acid residues 1 to 8 of SEQ ID NO:2.

In a preferred embodiment, a polypeptide or protein has an N-terminal cytoplasmic domain or a region which includes at least about 5, preferably about 1 to 10, and more preferably about 1 to 8 amino acid residues and has at least about 60%, 70% 80% 90% 95%, 99%, or 100% homology with an "N-terminal cytoplasmic domain," e.g., the N-terminal cytoplasmic domain of human 47153 (e.g., residues 1 to 8 of SEQ ID NO:2).

In another embodiment, a cytoplasmic region of a 47153 protein can include the C-terminus and can be a "C-terminal cytoplasmic domain," also referred to herein as a "C-terminal cytoplasmic tail." As used herein, a "C-terminal cytoplasmic domain" includes an amino acid sequence having a length of at least about 50, preferably about 1 to 100, more preferably about 1 to 84 amino acid residues and is located inside of a cell or within the cytoplasm of a cell. The N-terminal amino acid residue of a "C-terminal cytoplasmic domain" is adjacent to a C-terminal amino acid residue of a transmembrane domain in a 47153 protein. For example, a C-terminal cytoplasmic domain is located at about amino acid residues 360 to 443 of SEQ ID NO:2.

In a preferred embodiment, a 47153 polypeptide or protein has a C-terminal cytoplasmic domain or a region which includes at least about 5, preferably about 1 to 100, and more preferably about 1 to 84 amino acid residues and has at least about 60%, 70% 80% 90% 95%, 99%, or 100% homology with a C-terminal cytoplasmic domain," e.g., the C-terminal cytoplasmic domain of human 47153 (e.g., residues 360 to 443 of SEQ ID NO:2).

In another embodiment, a 47153 protein includes at least one non-cytoplasmic loops. As used herein, a "non-cytoplasmic loop" includes an amino acid sequence located outside of a cell or within an intracellular organelle. Non-cytoplasmic loops include extracellular domains (i.e., outside of the cell) and intracellular domains (i.e., within the cell). When referring to membrane-bound proteins found in intracellular organelles (e.g., mitochondria, endoplasmic reticulum, peroxisomes microsomes, vesicles, endosomes, and lysosomes), non-cytoplasmic loops include those domains of the protein that reside in the lumen of the organelle or the matrix or the intermembrane space. For example, a "non-cytoplasmic loop" can be found at about amino acid residues 28 to 342 of SEQ ID NO:2.

In a preferred embodiment, a 47153 polypeptide or protein has at least one non-cytoplasmic loop or a region which includes at least about 4, preferably about 5 to 350, more preferably about 6 to 314 amino acid residues and has at least about 60%, 70% 80% 90% 95%, 99%, or 100% homology with a "non-cytoplasmic loop," e.g., at least one non-cytoplasmic loop of human 47153 (e.g., residues 28 to 342 of SEQ ID NO:2).

A 47153 family member can include at least one glycosyltransferase domain; and at least one, preferably two transmembrane or non-transmembrane domains. Furthermore, a 47153 family member can include at least one N-glycosylation site (PS00001); at least one cAMP/cGMP protein kinase phosphorylation site (PS00004); at least one, two, three, four, preferably five protein kinase C phosphorylation sites (PS00005); at least one, two, three, and preferably four casein kinase II phosphorylation sites (PS00006); at least one, two, three, four, five, and preferably six N-myristoylation sites (PS00008); at least one amidation site (PS00009); or at least one peroxisomal targeting signal.

As the 47153 polypeptides of the invention can modulate 47153-mediated activities, they can be useful for developing novel diagnostic and therapeutic agents for glycosyltransferase-associated or other 47153-associated disorders, as described below.

As used herein, a "glycosyltransferase-mediated activity" includes an activity that involves the synthesis of glycoconjugates. For example, a "glycosyltransferase-mediated activity" can be an activity that involves 1) the transfer of an activated sugar residue to an acceptor molecule; 2) the processing, folding, and secretion of proteins; 3) the modulation of tumor cell growth and invasion; 4) myelin formation; 5) signal transduction; 6) viral and microbial adhesion; 7) oligodendrocyte development; 8) sperm-egg binding; 9) evasion of immune detection; 10) xenograft rejection; and 11) the ability to antagonize or inhibit, competitively or non-competitively, any of 1–11.

As used herein, a "47153 activity", "biological activity of 47153" or "functional activity of 47153", refers to an activity exerted by a 47153 protein, polypeptide or nucleic acid molecule on e.g., a 47153-responsive cell or on a 47153 substrate, e.g., a protein substrate, as determined in vivo or in vitro. In one embodiment, a 47153 activity is a direct activity, such as an association with a 47153 target molecule. A "target molecule" or "binding partner" is a molecule with which a 47153 protein binds or interacts in nature. In an exemplary embodiment, 47153 is an enzyme for the synthesis of glycoconjugates, including glycolipids, glycoproteins, and polysaccharides, by transferring an activated mono- or oligosaccharide residue to an existing acceptor molecule for the initiation or elongation of the carbohydrate chain. In an exemplary embodiment, 47153 is an enzyme for a UDP-glucose, UDP-N-acetyl-galactosamine, GDP-mannose or CDP-abequose substrate.

A 47153 activity can also be an indirect activity, e.g., a cellular signaling activity mediated by interaction of the 47153 protein with a 47153 receptor. Based on the above-described sequence structures and similarities to molecules of known function, the 47153 molecules of the present invention have similar biological activities as glycosyltransferase family members. For example, the 47153 proteins of the present invention can have one or more of the following activities: 1) the transfer of an activated sugar residue to an acceptor molecule; 2) the processing, folding, and secretion of proteins; 3) the modulation of tumor cell growth and invasion; 4) myelin formation; 5) signal transduction; 6) viral and microbial adhesion; 7) oligodendrocyte development; 8) sperm-egg binding; 9) evasion of immune detection; 10) xenograft rejection; and 11) the ability to antagonize or inhibit, competitively or non-competitively, any of 1–11.

Further, as seen in Example 3, 47153 mRNA showed highest expression in the normal brain cortex, and as such, it is expected that activators or inhibitors of 47153 molecules will be useful in treating brain disorders.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states-global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-bome (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin B1) deficiency and vitamin B12 deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The 47153 protcin, fragments thereof, and derivatives and other variants of the sequence in SEQ ID NO:2 thereof are collectively referred to as "polypeptides or proteins of the invention" or "47153 polypeptides or proteins". Nucleic acid molecules encoding such polypeptides or proteins are collectively referred to as "nucleic acids of the invention" or "47153 nucleic acids."

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) *John Wiley & Sons*, N.Y., 6.3.1–6.3.6, which is incorporated by reference. Aqueous and nonaqueolts methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS, at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 47153 protein, preferably a mammalian 47153 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 47153 protein having less than about 30%. 20%, 10% and more preferably 5% (by dry weight), of non-47153 protein (also referred to herein as a "contaminating protein"), or of chemical precursors or non-47153 chemicals. When the 47153 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 47153 (e.g., the sequence of SEQ D NO: 1 or 3) without abolishing or more preferably, without substantially altering a biological activity, whereas an "essential" amino acid residue results in such a change. For example, amino acid residues that are conserved among the polypeptides of the present invention, e.g., those present in the glycosyltransferase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serinc, threonine, tyrosine, cysteine), nonpolar side chains (e.g., alanine, valine, leucine, isoleucine, proline, phenylalanine, methionine, tryptoplian), beta-branched side chains (e.g., threonine, valine, isoleucine) and aromatic side chains (e.g., tyrosine, phenylalanine, tryptophan, histidine). Thus, a predicted nonessential amino acid residue in a 47153 protein is preferably replaced with another amino acid residue from the same side chain family. Alternatively, in another embodiment, mutations can be introduced randomly along all or part of a 47153 coding sequence, such as by saturation mutagenesis, and the resultant mutants can be screened for 47153 biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a 47153 protein includes a fragment of a 47153 protein which participates in an interaction between a 47153 molecule and a non-47153 molecule. Biologically active portions of a 47153 protein include peptides comprising amino acid sequences sufficiently homologous to or derived from the amino acid sequence of the 47153 protein, e.g., the amino acid sequence shown in SEQ ID NO:2, which include fewer amino acids than the full length 47153 protein, and exhibit at least one activity of a 47153 protein. Typically, biologically active portions comprise a domain or motif with at least one activity of the 47153 protein, e.g., glycosyltransferase activity. A biologically active portion of a 47153 protein can be a polypeptide which is, for example, 10, 25, 50, 100, 200 or more amino acids in length. Biologically active portions of a 47153 protein can be used as targets for developing agents which modulate a 47153 mediated activity, e.g., activity associated with catalyzing the synthesis of glycoconjugates.

Calculations of homology, or sequence identity (the terms "homology" and "identity" are used interchangeably herein) between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 47153 amino acid sequence of SEQ ID NO:2 having 443 amino acid residues, at least about 133, preferably at least about 178, more preferably at least about 222, even more preferably at least about 266, and even more preferably at least about 311, 355, or 400 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity betven two amino acid or nucleotide sequences can be determined using the algorithm of E. Meyers and W. Miller ((1989) CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 47153 nucleic acid molecules of the invention. BLAST protein searches can be performed with the XBLAST program, score=50, wordlength=3 to obtain amino acid sequences homologous to 47153 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See www.nebi.nlm.nih.gov.

Particular 47153 polypeptides of the present invention have an amino acid sequence substantially identical to the amino acid sequence of SEQ ID NO:2. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For ex ample, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%, 91%, 92%, 93%, 94%, 95%, 96%, 97%, 98% or 99% identity to SEQ ID NO:1 or 3 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 47153 polypeptide described herein, e.g., a full length 47153 protein or a fragment thereof, e.g., a biologically active portion of 47153 protein. Also included is a nucleic acid fragment suitable for use as a hybridization probe, which can be used, e.g., to identify a nucleic acid molecule encoding a polypeptide of the invention, 47153 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of this nucleotide sequence. In one embodiment, the nucleic acid molecule includes sequences encoding the human 47153 protein (i.e., "the coding region" of SEQ ID NO:1, as shown in SEQ ID NO:3), as well as 5' untranslated sequences (nucleotides 1 to 310 of SEQ ID NO:1) and 3' untranslated sequences (nucleotides 1646 to 1788 of SEQ ID NO:1). Alternatively, the nucleic acid molecule can include only the coding region of SEQ ID NO:1 (e.g., SEQ ID NO:3) and, e.g., no flanking sequences which normally accompany the subject sequence. In another embodiment, the nucleic acid molecule encodes a sequence corresponding to a fragment of the protein from about amino acid 137 to 323 of SEQ ID NO:2.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3 such that it can hybridize to the nucleotide sequence shown in SEQ ID NO:1 or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or SEQ ID NO:3, or a portion, preferably of the same length, of any of these nucleotide sequences.

47153 Nucleic Acid Fragments

A nucleic acid molecule of the inverition can include only a portion of the nucleic acid sequence of SEQ ID NO:1 or 3. For example, such a nucleic acid molecule can include a fragment which can be used as a probe or primer or a fragment encoding a portion of a 47153 protein, e.g., an immunogenic or biologically active portion of a 47153 protein. A fragment can comprise those nucleotides of SEQ ID NO:1, which encode a glycosyltransferase domain of human 47153. The nucleotide sequence determined from the cloning of the 47153 gene allows for the generation of probes and primers designed for use in identifying and/or cloning other 47153 family members, or fragments thereof, as well as 47153 homologs, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 100 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 47153 nucleic acid fragment can include a sequence corresponding to a glycosyltransferase domain, as described herein.

47153 probes and primers are provided Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes:
  a glycosyltransferase domain from about amino acid residues 11 to 98, 137 to 323, 167 to 223 or 212 to 247 in SEQ ID NO:2 or an N-acetylgalactosaminyltransferase from about amino acid residues 135 to 282, 299 to 436, 329 to 387 or 388 to 436 in SEQ ID NO.2.

In another embodiment a set of primers is provided, e.g., primers suitable for use in a PCR, which can be used to amplify a selected region of a 47153 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant. For example, primers suitable for amplifying all or a portion of any of the following regions are provided: a glycosyltransferase domain from about amino acid 137 to 323 of SEQ ID NO:2 or an N-acetylgalactosaminyltransferase domain from about amino acid residues 135 to 282 or 299 to 436 in SEQ ID NO.2.

A nucleic acid fragment can encode an epitope bearing region of a polypeptide described herein.

A nucleic acid fragment encoding a "biologically active portion of a 47153 polypeptide" can be prepared by isolating a portion of the nucleotide sequence of SEQ ID NO:1 or 3, which encodes a polypeptide having a 47153 biological activity (e.g., the biological activities of the 47153 proteins are described herein), expressing the encoded portion of the 47153 protein (e.g., by recombinant expression in vitro) and assessing the activity of the encoded portion of the 47153 protein. For example, a nucleic acid fragment encoding a biologically active portion of 47153 includes a glycosyltransferase domain, e.g., amino acid residues about 137 to 323 of SEQ ID NO:2. A nucleic acid fragment encoding a biologically active portion of a 47153 polypeptide, can comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400, 1495, 1500, 1600, 1700 or more nucleotides in length and hybridizes under stringent hybridization conditions to a nucleic acid molecule of SEQ ID NO:1 or SEQ ID NO:3.

47153 Nucleic Acid Variants

The invention further encompasses nucleic acid molecules that differ from the nucleotide sequence shown in SEQ ID NO:1 or SEQ ID NO:3. Such differences can be due to degeneracy of the genetic code (and result in a nucleic acid which encodes the same 47153 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at vleast one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or 3, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2 or a fragment of this sequence. Such nucleic acid molecules can readily be identified as being able to hybridize under stringent conditions, to the nucleotide sequence shown in SEQ ID NO 2 or a fragment of the sequence. Nucleic acid molecules corresponding to orthologs, homologs, and allelic variants of the 47153 cDNAs of the invention can further be isolated by mapping to the same chromosome or locus as the 47153 gene.

Preferred variants include those that are correlated with catalyzing the synthesis of glycoconjugates.

Allelic variants of 47153, e.g., human 47153, include both functional and non-functional proteins. Functional allelic variants are naturally occurring amino acid sequence variants of the 47153 protein within a population that maintain the ability to catalyze the synthesis of glycoconjugates. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 47153, e.g., human 47153, protein within a population that do not have the ability to catalyze the synthesis of glycoconjugates. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 47153 family members and, thus, which have a nucleotide sequence which differs from the 47153 sequences of SEQ ID NO:1 or SEQ ID NO:3 are intended to be within the scope of the invention.

Antisense Nucleic Acid Molecules, Ribozymes and Modified 47153 Nucleic Acid Molecules In another aspect, the invention features, an isolated nucleic acid molecule which is antisense to 47153. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 47153 coding strand, or to only a portion thereof (e.g., the coding region of human 47153 corresponding to SEQ ID NO:3). In another embodiment, the antisense nucleic acid molecule is antisense to a "noncoding region" of the coding strand of a nucleotide sequence encoding 47153 (e.g., the 5' and 3' untranslated regions).

An antisense nucleic acid can be designed such that it is complementary to the entire coding region of 47153 mRNA, but more preferably is an oligonucleotide which is antisense to only a portion of the coding or noncoding region of 47153 mRNA. For example, the antisense oligonucleotide can be complementary to the region surrounding the translation start site of 47153 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 47153 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically or selectively bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual P-units, the strands run parallel to each other (Gaultier et al. (1987) *Nucleic Acids. Res.* 15:6625–6641). The antisense nucleic acid molecule can also comprise a 2′-o-methylribonucleotide (Inoue et al. *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 47153-encoding nucleic acid can include one or more sequences complementary to the nucleotide sequence of a 47153 cDNA disclosed herein (i.e., SEQ ID NO:1 or SEQ ID NO:3), and a sequence having known catalytic sequence responsible for mRNA cleavage (see U.S. Pat. No. 5,093,246 or Haselhoff and Gerlach (1988) *Nature* 334:585–591). For example, a derivative of a *Tetrahymena* L-19 IVS RNA can be constructed in which the nucleotide sequence of the active site is complementary to the nucleotide sequence to be cleaved in a 47153-encoding mRNA. See, e.g., Cech et al. U.S. Pat. No. 4,987,071; and Cech et al. U.S. Pat. No. 5,116,742. Alternatively, 47153 mRNA can be used to select a catalytic RNA having a specific ribonuclease activity from a pool of RNA molecules. See, e.g., Bartel, D. and Szostak, J. W. (1993) *Science* 261:1411–1418.

47153 gene expression can be inhibited by targeting nucleotide sequences complementary to the regulatory region of the 47153 (e.g., the 47153 promoter and/or enhancers) to form triple helical structures that prevent transcription of the 47153 gene in target cells. See generally, Helene, C. (1991) *Anticancer Drug Des.* 6:569–84; Helene, C. (1992) *Ann. N.Y. Acad. Sci.* 660:27–36; and Maher, L. J. (1992) *Bioassays* 14:807–15. The potential sequences that can be targeted for triple helix formation can be increased by creating a so-called "switchback" nucleic acid molecule. Switchback molecules are synthesized in an alternating 5′-3′,3′-5′ manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 47153 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et a!. (1996) *Bioorganic & Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-OKeefe et a.l (1996) *Proc. Natl. Acad. Sci.* 93: 14670–675.

PNAs of 47153 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 47153 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-OKeefe supra).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 47153 nucleic acid of the invention, two complementary regions one having a fluorophore and one a quencher such that the molecular beacon is useful for quantitating the presence of the 47153 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 47153 Polypeptides

In another aspect, the invention features, an isolated 47153 protein, or fragment, e.g., a biologically active portion, for use as immunogens or antigens to raise or test (or more generally to bind) anti-47153 antibodies. 47153 protein can be isolated from cells or tissue sources using standard protein purification techniques. 47153 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present in a native cell.

In a preferred embodiment, a 47153 polypeptide has one or more of the following characteristics:

it has the ability to catalyze the synthesis of glycoconjugates;

it has a molecular weight, e.g., a deduced molecular weight, preferably ignoring any contribution of post translational modifications, amino acid composition or other physical characteristic of a 47153 polypeptide, e.g., a polypeptide of SEQ ID NO:2;

it has an overall sequence similarity of at least 60%, preferably at least 70%, more preferably at least 80, 90, or 95%, with a polypeptide of SEQ ID NO:2;

it has a glycosyltransferase domain which is preferably about 70%, 80%, 90% or 95% identical to amino acid residues about 11 to 98, about 137 to 323, about 167 to 223, or about 212 to 247 of SEQ ID NO:2;

it has at least 1, preferably 4, and most preferably 7 of the cysteines found amino acid sequence of the native protein; or it has an N-acetylgalactosaminyltransferase domain which is preferably about 70%, 80%, 90% or 95% identical to amino acid residues 135 to 282, 255 to 326, 299 to 436, 329 to 387 or 388 to 436 in SEQ ID NO.2.

In a preferred embodiment the 47153 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the glycosyltransferase domain, that is amino acid residues 1–136 and 324–443. In another embodiment one or more differences are in the glycosyltransferase domain, that is amino acid residues 137–323.

Other embodiments include a protein that contains one or more changes in amino acid sequence, e.g., a change in an amino acid residue which is not essential for activity. Such 47153 proteins differ in amino acid sequence from SEQ ID NO:2, yet retain biological activity.

In one embodiment, the protein includes an amino acid sequence at least about 60%, 65%, 70%, 75%, 80%, 85%, 90%, 95%, 98% or more homologous to SEQ ID NO:2.

A 47153 protein or fragment is provided which varies from the sequence of SEQ ID NO:2 in regions defined by amino acids outside the glycosyltransferase domain by at least one but by less than 15, 10 or 5 amino acid residues in the protein or fragment but which does not differ from SEQ ID NO:2 in regions defined by a glycosyltransferase domain. In some embodiments the difference is at a non-essential residue or is a conservative substitution, while in others the difference is at an essential residue or is a non-conservative substitution.

In one embodiment, a biologically active portion of a 47153 protein includes a glycosyltransferase domain. Moreover, other biologically active portions, in which other regions of the protein are deleted, can be prepared by recombinant techniques and evaluated for one or more of the functional activities of a native 47153 protein.

In a preferred embodiment, the 47153 protein has an amino acid sequence shown in SEQ ID NO:2. In other embodiments, the 47153 protein is sufficiently or substantially identical to SEQ ID NO:2. In yet another embodiment, the 47153 protein is sufficiently or substantially identical to SEQ ID NO:2 and retains the functional activity of the protein of SEQ ID NO:2, as described in detail in the subsections above.

47153 Chimeric or Fusion Proteins

In another aspect, the invention provides 47153 chimeric or fusion proteins. As used herein, a 47153 "chimeric protein" or "fusion protein" includes a 47153 polypeptide linked to a non-47153 polypeptide. A "non-47153 polypeptide" refers to a polypeptide having an amino acid sequence corresponding to a protein which is not substantially homologous to the 47153 protein, e.g., a protein which is different from the 47153 protein and which is derived from the same or a different organism. The 47153 polypeptide of the fusion protein can correspond to all or a portion e.g., a fragment described herein of a 47153 amino acid sequence. In a preferred embodiment, a 47153 fusion protein includes at least one (or two) biologically active portion of a 47153 protein. The non47153 polypeptide can be fused to the N-terminus or C-terminus of the 47153 polypeptide.

The fusion protein can include a moiety which has a high affinity for a ligand. For example, the fusion protein can be a GST-47153 fusion protein in which the 47153 sequences are fused to the C-terminus of the GST sequences. Such fusion proteins can facilitate the purification of recombinant 47153. Alternatively, the fusion protein can be a 47153 protein containing a heterologous signal sequence at its N-terminus. In certain host cells (e.g., mammalian host cells), expression and/or secretion of 47153 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge C1 and C2 sequences of an immunoglobulin or human serum albumin.

The 47153 fusion proteins of the invention can be incorporated into pharmaceutical compositions and administered to a subject in vivo. The 47153 fusion proteins can be used to affect the bioavailability of a 47153 substrate. 47153 fusion proteins can be useful therapeutically for the treatment of disorders caused by, for example, (i) aberrant modification or mutation of a gene encoding a 47153 protein; (ii) mis-regulation of the 47153 gene; and (iii) aberrant post-translational modification of a 47153 protein.

Moreover, the 47153-fusion proteins of the invention can be used as immunogens to produce anti-47153 antibodies in a subject, to purify 47153 ligands and in screening assays to identify molecules which inhibit the interaction of 47153 with a 47153 substrate.

Expression vectors are commercially available that already encode a fusion moiety (e.g., a GST polypeptide). A 47153-encoding nucleic acid can be cloned into such an expression vector such that the fusion moiety is linked in-frane to the 47153 protein.

Variants of 47153 Proteins

In another aspect, the invention also features a variant of a 47153 polypeptide, e.g., which functions as an agonist (mimetics) or as an antagonist. Variants of the 47153 proteins can be generated by mutagenesis, e.g., discrete point mutation, the insertion or deletion of sequences or the truncation of a 47153 protein. An agonist of the 47153 proteins can retain substantially the same, or a subset, of the biological activities of the naturally occurring form of a 47153 protein. An antagonist of a 47153 protein can inhibit one or more of the activities of the naturally occurring form of the 47153 protein by, for example, competitively modulating a 47153-mediated activity of a 47153 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 47153 protein.

Variants of a 47153 protein can be identified by screening combinatorial libraries of mutants, e.g., truncation mutants, of a 47153 protein for agonist or antagonist activity.

Libraries of fragments e.g., N terminal, C terminal, or internal fragments, of a 47153 protein coding sequence can be used to generate a variegated population of fragments for screening and subsequent selection of variants of a 47153 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 47153 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated 47153 library. For example, a library of expression vectors can be transfected into a cell line, e.g., a cell line, which ordinarily responds to 47153 in a substrate-dependent manner. The transfected cells are then contacted with 47153 and the effect of the expression of the mutant on signaling by the 47153 substrate can be detected, e.g., by measuring the ability to catalyze the synthesis of glycoconjugates. Plasmid DNA can then be recovered from the cells which score for inhibition, or alternatively, potentiation of signaling by the 47153 substrate, and the individual clones further characterized.

In another aspect, the invention features a method of making a 47153 polypeptide, e g., a peptide having a non-wild type activity, e.g., an antagonist, agonist, or super agonist of a naturally occurring 47153 polypeptide, e.g., a naturally occurring 47153 polypeptide. The method includes altering the sequence of a 47153 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 47153 polypeptide a biological activity of a naturally occurring 47153 polypeptide. The method includes altering the sequence, e.g., by substitution or deletion of one or more residues, of a 47153 polypeptide, e.g., altering the sequence of a non-conserved region, or a domain or residue described herein, and testing the altered polypeptide for the desired activity.

Anti-47153 Antibodies

In another aspect, the invention provides an anti-47153 antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and F(ab')$_2$ fragments which can be generated by treating the antibody with an enzyme such as papain or pepsin, respectively.

The antibody can be a polyclonal, monoclonal, recombinant, e.g., a chimeric or humanized, fully hurnan, non-human, e.g., murine, or single chain antibody. In a preferred embodiment it has effector function and can fix complement. The antibody can be coupled to a toxin or imaging agent.

A full-length 47153 protein or, antigenic peptide fragment of 47153 can be used as an immunogen or can be used to identify anti47153 antibodies made with other immunogens, e.g., cells, membrane preparations, and the like. The antigenic peptide of 47153 should include at least 8 amino acid residues of the amino acid sequence shown in SEQ ID NO:2 and encompasses an epitope of 47153. Preferably, the antigenic peptide includes at least 10 amino acid residues, more preferably at least 15 amino acid residues, even more preferably at least 20 amino acid residues, and most preferably at least 30 amino acid residues.

Fragments of 47153 which include residues about 85 to 100, from about 180 to 200, and from about 280 to 300 of SEQ ID NO:2 can be used to make, e.g., used as immunogens or used to characterize the specificity of an antibody, antibodies against hydrophilic regions of the 47153 protein (see FIG. 2). Similarly, fragments of 47153 which include residues about 100 to 110, from about 250 to 260, and from about 340 to 360 of SEQ ID NO:2 can be used to make an antibody against a hydrophobic region of the 47153 protein; fragments of 47153 which include residues about 28 to 342 SEQ ID NO:2 can be used to make an antibody against a non-cytoplasmic region of the 47153 protein; fragments of 47153 which include residues about 1 to 8 or about 360 to 443 of SEQ ID NO:2 can be used to make an antibody against an intracellular region of the 47153 protein; a fragment of 47153 which include residues about 11 to 98, about 137 to 323, about 135 to 282, about 167 to 223, about 212 to 247, about 255 to 326, about 299 to 436, about 329 to 387, or about 388 to 436 of SEQ ID NO:2 can be used to make an antibody against the glycosyltransferase or N-acetylgalactosaminyltransferase region of the 47153 protein.

Antibodies reactive with, or specific or selective for, any of these regions, or other regions or domains described herein are provided.

Preferred epitopes encompassed by the antigenic peptide are regions of 47153 located on the surface of the protein, e.g., hydrophilic regions, as well as regions with high antigenicity. For example, an Emini surface probability analysis of the human 47153 protein sequence can be used to indicate the regions that have a particularly high probability of being localized to the surface of the 47153 protein and are thus likely to constitute surface residues useful for targeting antibody production.

In a preferred embodiment the antibody can bind to the extracellular portion of the 47153 protein, e.g., it can bind to a whole cell which expresses the 47153 protein. In another embodiment, the antibody binds an intracellular portion of the 47153 protein.

In a preferred embodiment the antibody binds an epitope on any domain or region on 47153 proteins described herein.

Additionally, chimeric, humanized, and completely human antibodies are also within the scope of the invention. Chimeric, humanized, but most preferably, completely human antibodies are desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446449; and Shaw et al. (1988) *J. Nat. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

The anti-47153 antibody can be a single chain antibody. A single-chain antibody (scFV) can be engineered (see, for example, Colcher, D. et al. (1999) *Ann. N Y Acad. Sci.* 880:263–80; and Reiter, Y. (1996) *Clin. Cancer Res.* 2:245–52). The single chain antibody can be dimerized or multimerized to generate multivalent antibodies having specificities for different epitopes of the same target 47153 protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region. An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("1L-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-47153 antibody (e.g., monoclonal antibody) can be used to isolate 47153 by standard techniques, such as affinity chromatography or immunoprecipitation. Moreover, an anti-47153 antibody can be used to detect 47153 protein (e.g., in a cellular lysate or cell supernatant) in order to evaluate the abundance and pattern of expression of the protein. Anti-47153 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In preferred embodiments, an antibody can be made by immunizing with a purified 47153 antigen, or a fragment thereof, e.g., a fragment described herein, a membrane associated antigen, tissues, e.g., crude tissue preparations, whole cells, preferably living cells, lysed cells, or cell fractions, e.g., membrane fractions.

Antibodies which bind only a native 47153 protein, only denatured or otherwise non-native 47153 protein, or which bind both, are within the invention. Antibodies with linear or conformational epitopes are within the invention. Conformational epitopes sometimes can be identified by identifying antibodies which bind to native but not denatured 47153 protein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 47153 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 47153 proteins, mutant forms of 47153 proteins, fusion proteins, and the like).

The recombinant expression vectors of the invention can be designed for expression of 47153 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 47153 activity assays, (e.g., direct assays or competitive assays described in detail below), or to generate antibodies specific or selective for 47153 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 47153 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, *cytomegalovirus* and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Baneriji et al. (1983) *Cell* 33:729–740; Queen and Baltimore (1983) *Cell* 33:741–748), neuron-specific promoters (e.g., the neurofilament promoter; Byrne and Ruddle (1989) *Proc. Nat. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., (1986) *Reviews—Trends in Genetics* 1:1.

Another aspect the invention provides a host cell which includes a nucleic acid molecule described herein, e.g., a 47153 nucleic acid molecule within a recombinant expression vector or a 47153 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic or eukaryotic cell. For example, a 47153 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 47153 protein. Accordingly, the invention further provides methods for producing a 47153 protein using the host cells of the invention. In one embodiment, the method includes culturing the host cell of the invention (into which a recombinant expression vector encoding a 47153 protein has been introduced) in a suitable medium such that a 47153 protein is produced. In another embodiment, the method further includes isolating a 47153 protein from the medium or the host cell.

In another aspect, the invention features, a cell or purified preparation of cells which include a 47153 transgene, or which otherwise misexpress 47153. The cell preparation can consist of human or non-human cells, e.g., rodent cells, e.g., mouse or rat cells, rabbit cells, or pig cells. In preferred embodiments, the cell or cells include a 47153 transgene, e.g., a heterologous form of a 47153, e.g., a gene derived from humans (in the case of a non-human cell). The 47153 transgene can be misexpressed, e.g., overexpressed or underexpressed. In other preferred embodiments, the cell or cells include a gene which misexpresses an endogenous 47153, e.g., a gene the expression of which is disrupted, e.g., a knockout. Such cells can serve as a model for studying disorders which are related to mutated or misexpressed 47153 alleles or for use in drug screening.

In another aspect, the invention features, a human cell, e.g., a hematopoietic stem cell, transformed with nucleic acid which encodes a subject 47153 polypeptide.

Also provided are cells, preferably human cells, e.g., human hematopoietic or fibroblast cells, in which an endogenous 47153 is under the control of a regulatory sequence that does not normally control the expression of the endogenous 47153 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 47153 gene. For example, an endogenous 47153 gene which is "transcriptionally silent," e.g., not normally expressed, or expressed only at very low levels, can be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 47153 protein and for identifying and/or evaluating modulators of 47153 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 47153 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 47153 protein to particular cells. A transgenic founder animal can be identified based upon the presence of a 47153 transgene in its genome and/or expression of 47153 mRNA in tissues or cells of the animals. A transgenic founder animal can then be used to breed additional animals carrying the transgene. Moreover, transgenic animals carrying a transgene encoding a 47153 protein can further be bred to other transgenic animals carrying other transgenes.

47153 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologs, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 47153 protein (e.g., via a recombinant expression vector in a host cell in gene therapy applications), to detect a 47153 mRNA (e.g., in a biological sample) or a genetic alteration in a 47153 gene, and to modulate 47153 activity, as described further below. The 47153 proteins can be used to treat disorders characterized by insufficient or excessive production of a 47153 substrate or production of 47153 inhibitors. In addition, the 47153 proteins can be used to screen for naturally occurring 47153 substrates, to screen for drugs or compounds which modulate 47153 activity, as well as to treat disorders characterized by insufficient or excessive production of 47153 protein or production of 47153 protein forms which have decreased, aberrant or unwanted activity compared to 47153 wild type protein (e.g., aberrant or deficient 47153-associated function). Moreover, the anti47153 antibodies of the invention can be used to detect and isolate 47153 proteins, regulate the bioavailability of 47153 proteins, and modulate 47153 activity.

A method of evaluating a compound for the ability to interact with, e.g., bind, a subject 47153 polypeptide is provided. The method includes: contacting the compound with the subject 47153 polypeptide; and evaluating ability of the compound to interact with, e.g., to bind or form a complex with the subject 47153 polypeptide. This method can be performed in vitro, e.g., in a cell free system, or in vivo, e.g., in a two-hybrid interaction trap assay. This method can be used to identify naturally occurring molecules which interact with subject 47153 polypeptide. It can also be used to find natural or synthetic inhibitors of subject 47153 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to 47153 proteins, have a stimulatory or inhibitory effect on, for example, 47153 expression or 47153 activity, or have a stimulatory or inhibitory effect on, for example, the expression or activity of a 47153 substrate. Compounds thus identified can be used to modulate the activity of target gene products (e.g., 47153 genes) in a therapeutic protocol, to elaborate the biological function of the target gene product, or to identify compounds that disrupt normal target gene interactions.

In one embodiment, the invention provides assays for screening candidate or test compounds which are substrates of a 47153 protein or polypeptide or a biologically active portion thereof. In another embodiment, the invention provides assays for screening candidate or test compounds which bind to or modulate the activity of a 47153 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909–13; Erb et al. (1994) *Proc. Natl. Acad. Sci. USA* 91:11422–426; Zuckermann et al. (1994). *J. Med. Chem.* 37:2678–85; Cho et al. (1993) *Science* 261:1303; Carrell et al (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233–51.

Libraries of compounds can be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390; Devlin (1990) *Science* 249:404406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a 47153 protein or biologically active portion thereof is contacted with a test compound, and the ability of the test compound to modulate 47153 activity is determined. Determining the ability of the test compound to modulate 47153 activity can be accomplished by monitoring, for example, the ability to catalyze the synthesis of glycoconjugates. The cell, for example, can be of mammalian origin, e.g., human.

The ability of the test compound to modulate 47153 binding to a compound, e.g., a 47153 substrate, or to bind to 47153 can also be evaluated. This can be accomplished, for example, by coupling the compound, e.g., the substrate, with a radioisotope or enzymatic label such that binding of the compound, e.g., the substrate, to 47153 can be determined by detecting the labeled compound, e.g., substrate, in a complex. Alternatively, 47153 could be coupled with a radioisotope or enzymatic label to monitor the ability of a test compound to modulate 47153 binding to a 47153 substrate in a complex. For example, compounds (e.g., 47153 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 47153 substrate) to interact with 47153 with or without the labeling of any of the interactants can be evaluated. For example, a microphysiometer can be used to detect the interaction of a compound with 47153 without the labeling of either the compound or the 47153. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 47153.

In yet another embodiment, a cell-free assay is provided in which a 47153 protein or biologically active portion thereof is contacted with a test compound and the ability of the test compound to bind to the 47153 protein or biologically active portion thereof is evaluated. Preferred biologically active portions of the 47153 proteins to be used in assays of the present invention include fragments which participate in interactions with non-47153 molecules, e.g., fragments with high surface probability scores.

Soluble and/or membrane-bound forms of isolated proteins (e.g., 47153 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton®X-100, Triton®X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-bydroxy-1-propane sulfonate (CHAPSO), or N-dodecyl=N, N-diethyl-3-amnonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 47153 protein to bind to a target molecule can be accomplished using real-time Biomolecular Interaction Analysis (BIA) (see, e.g., Sjolander, S. and Urbaniczky, C. (1991) Anal. Chem. 63:2338–2345 and Szabo et at. (1995) Curr. Opin. Struct. Biol. 5:699–705). "Surface plasmon resonance" or "BIA" detects biospecific interactions in real time, without labeling any of the interactants (e.g., BLAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 47153, an anti-47153 antibody or its target molecule to facilitate separation of complexed from uncomplexed forms of one or both of the proteins, as well as to accommodate automation of the assay. Binding of a test compound to a 47153 protein, or interaction of a 47153 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/47153 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 47153 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 47153 binding or activity determined using standard techniques.

Other techniques for immobilizing either a 47153 protein or a target molecule on matrices include using conjugation of biotin and streptavidin. Biotinylated 47153 protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific or selective for the immobilized component (the antibody, in turn, can be directly labeled or indirectly labeled with, e.g., a labeled anti-Ig antibody).

In one embodiment, this assay is performed utilizing antibodies reactive with 47153 protein or target molecules but which do not interfere with binding of the 47153 protein to its target molecule. Such antibodies can be derivatized to the wells of the plate, and unbound target or 47153 protein trapped in the wells by antibody conjugation. Methods for detecting such complexes, in addition to those described above for the GST-immobilized complexes, include immunodetection of complexes using antibodies reactive with the 47153 protein or target molecule, as well as enzyme-linked assays which rely on detecting an enzymatic activity associated with the 47153 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. (1999) *Current Protocols in Molecular Biology*, J. Wiley, New York.); and immunoprecipitation (see, for example, Ausubel, F. et al., eds. (1999) *Current Protocols in Molecular Biology*, J. Wiley, New York). Such resins and chromatographic techniques are known to one skilled in the art (see, e.g., Heegaard, N. H., (1998) *J Mol Recognit* 11:141–8; Hage, D. S., and Tweed, S. A. (1997) *J Chromatogr B Biomed Sci Appi.* 699:499–525). Further, fluorescence energy transfer can also be conveniently utilized, as described herein, to detect binding without further purification of the complex from solution.

In a preferred embodiment, the assay includes contacting the 47153 protein or biologically active portion thereof with a known compound which binds 47153 to form an assay mixture, contacting the assay mixture with a test compound, and determining the ability of the test compound to interact with a 47153 protein, wherein determining the ability of the test compound to interact with a 47153 protein includes determining the ability of the test compound to preferentially bind to 47153 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners."Compounds that disrupt such interactions can be useful in regulating the activity of the target gene product. Such compounds can include, but are not limited to molecules such as antibodies, peptides, and small molecules. The preferred target genes/products for use in this embodiment are the 47153 genes herein identified. In an alternative embodiment, the invention provides methods for determining the ability of the test compound to modulate the activity of a 47153 protein through modulation of the activity of a downstream effector of a 47153 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form a complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific or selective for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific or selective for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific or selective for one of the binding components to anchor any complexes formed in solution, and a labeled antibody specific or selective for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 47153 proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biolechniques 14:920–924; Iwabuchi et al. (1993) Oncogene 8:1693–1696; and Brent WO94/10300), to identify other proteins, which bind to or interact with 47153 ("47153-binding proteins" or "47153-bp") and are involved in 47153 activity. Such 47153-bps can be activators or inhibitors of signals by the 47153 proteins or 47153 targets as, for example, downstream elements of a 47153-mediated signaling pathway.

The two-hybrid system is based on the modular nature of most transcription factors, which consist of separable DNA-binding and activation domains. Briefly, the assay utilizes two different DNA constructs. In one construct, the gene that codes for a 47153 protein is fused to a gene encoding the DNA binding domain of a known transcription factor (e.g., GAL4). In the other construct, a DNA sequence, from a library of DNA sequences, that encodes an unidentified protein ("prey" or "sample") is fused to a gene that codes for the activation domain of the known transcription factor. (Alternatively the: 47153 protein can be the fused to the activator domain.) If the "bait" and the "prey" proteins are able to interact, in vivo, forming a 47153-dependent complex, the DNA-binding and activation domains of the transcription factor are brought into close proximity. This proximity allows transcription of a reporter gene (e.g., lacz) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 47153 protein.

In another embodiment, modulators of 47153 expression are identified. For example, a cell or cell free mixture is contacted with a candidate compound and the expression of 47153 mRNA or protein evaluated relative to the level of expression of 47153 mRNA or protein in the absence of the candidate compound. When expression of 47153 mRNA or protein is greater in the presence of the candidate compound than in its absence, the candidate compound is identified as a stimulator of 47153 mRNA or protein expression. Alternatively, when expression of 47153 mRNA or protein is less (statistically significantly less) in the presence of the candidate compound than in its absence, the candidate compound is identified as an inhibitor of 47153 mRNA or protein expression. The level of 47153 mRNA or protein expression can be determined by methods described herein for detecting 47153 mRNA or protein.

In another aspect, the invention pertains to a combination of two or more of the assays described herein. For example, a modulating agent can be identified using a cell-based or a cell free assay, and the ability of the agent to modulate the activity of a 47153 protein can be confirmed in vivo, e.g., in an animal such as an animal model for aberrant or deficient 47153 associated function.

This invention further pertains to novel agents identified by the above-described screening assays. Accordingly, it is within the scope of this invention to further use an agent identified as described herein (e.g., a 47153 modulating agent, an antisense 47153 nucleic acid molecule, a 47153-specific antibody, or a 47153-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 47153 with a disease; (ii) identify an individual from a minute biological sample (tissue typing); and (iii) aid in forensic identification of a biological sample. These applications are described in the subsections below.

Chromosome Mapping

The 47153 nucleotide sequences or portions thereof can be used to map the location of the 47153 genes on a chromosome. This process is called chromosome mapping. Chromosome mapping is useful in correlating the 47153 sequences with genes associated with disease.

Briefly, 47153 genes can be mapped to chromosomes by preparing PCR primers (preferably 15–25 bp in length) from the 47153 nucleotide sequences. These primers can then be used for PCR screening of somatic cell hybrids containing individual human chromosomes. Only those hybrids containing the human gene corresponding to the 47153 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) Science 220:919–924).

Other mapping strategies e.g., in situ hybridization (described in Fan, Y. et al. (1990) Proc. Natl. Acad. Sci. USA, 87:6223–27), pre-screening with labeled flow-sorted chromosomes, and pre-selection by hybridization to chromosome specific cDNA libraries can be used to map 47153 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. (1988) Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (Such data are found, for example, in V. McKusick, *Mendelian Inheritance in Man*, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the 47153 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 47153 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 47153 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 47153 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 47153 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 47153 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 47153 probes can be used to identify tissue by species and/or by organ type.

In a similar fashion, these reagents, e.g., 47153 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 47153.

Such disorders include, e.g., a disorder associated with the misexpression of 47153 gene.

The method includes one or more of the following:

detecting, in a tissue of the subject, the presence or absence of a mutation which affects the expression of the 47153 gene, or detecting the presence or absence of a mutation in a region which controls the expression of the gene, e.g., a mutation in the 5' control region;

detecting, in a tissue of the subject, the presence or absence of a mutation which alters the structure of the 47153 gene;

detecting, in a tissue of the subject, the misexpression of the 47153 gene, at the mRNA level, e.g., detecting a non-wild type level of a mRNA;

detecting, in a tissue of the subject, the misexpression of the gene, at the protein level, e.g., detecting a non-wild type level of a 47153 polypeptide.

In preferred embodiments the method includes: ascertaining the existence of at least one of: a deletion of one or more nucleotides from the 47153 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the 47153 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 47153 gene; the presence of a non-wild type splicing pattern of a messenger RNA transcript of the gene; or a non-wild type level of 47153.

Methods of the invention can be used prenatally or to determine if a subject's offspring will be at risk for a disorder.

In preferred embodiments the method includes determining the structure of a 47153 gene, an abnormal structure being indicative of risk for the disorder.

In preferred embodiments the method includes contacting a sample from the subject with an antibody to the 47153 protein or a nucleic acid, which hybridizes specifically with the gene. These and other embodiments are discussed below.

Diagnostic and Prognostic Assays

The presence, level, or absence of 47153 protein or nucleic acid in a biological sample can be evaluated by obtaining a biological sample from a test subject and contacting the biological sample with a compound or an agent capable of detecting 47153 protein or nucleic acid (e.g., mRNA, genomic DNA) that encodes 47153 protein such that the presence of 47153 protein or nucleic acid is detected in the biological sample. The term "biological sample" includes tissues, cells and biological fluids isolated from a subject, as well as tissues, cells and fluids present within a subject. A preferred biological sample is serum. The level of expression of the 47153 gene can be measured in a number of ways, including, but not limited to: measuring the mRNA encoded by the 47153 genes; measuring the amount of protein encoded by the 47153 genes; or measuring the activity of the protein encoded by the 47153 genes.

The level of mRNA corresponding to the 47153 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 47153 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to 47153 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 47153 genes.

The level of mRNA in a sample that is encoded by one of 47153 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 47153 gene being analyzed.

In another embodiment, the methods further contacting a control sample with a compound or agent capable of detecting 47153 mRNA, or genomic DNA, and comparing the presence of 47153 mRNA or genomic DNA in the control sample with the presence of 47153 mRNA or genomic DNA in the test sample.

A variety of methods can be used to determine the level of protein encoded by 47153. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (ie., physically linking) a detectable substance to the probe or antibody, as well as indirect labeling of the probe or antibody by reactivity with a detectable substance. Examples of detectable substances are provided herein.

The detection methods can be used to detect 47153 protein in a biological sample in vitro as well as in vivo. In vitro techniques for detection of 47153 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 47153 protein include introducing into a subject a labeled anti-47153 antibody. For example, the antibody can be labeled with a radioactive marker whose presence and location in a subject can be detected by standard imaging techniques.

In another embodiment, the methods further include contacting the control sample with a compound or agent capable of detecting 47153 protein, and comparing the presence of 47153 protein in the control sample with the presence of 47153 protein in the test sample.

The invention also includes kits for detecting the presence of 47153 in a biological sample. For example, the kit can include a compound or agent capable of detecting 47153 protein or mRNA in a biological sample; and a standard. The compound or agent can be packaged in a suitable container. The kit can further comprise instructions for using the kit to detect 47153 protein or nucleic acid.

For antibody-based kits, the kit can include: (1) a first antibody (e.g. attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 47153 expression or activity. As used herein, the term "unwanted" includes an unwanted phenomenon involved in a biological response such as pain or deregulated cell proliferation.

In one embodiment, a disease or disorder associated with aberrant or unwanted 47153 expression or activity is identified. A test sample is obtained from a subject and 47153 protein or nucleic acid (e.g., mRNA or genomic DNA) is evaluated, wherein the level, e.g., the presence or absence, of 47153 protein or nucleic acid is diagnostic for a subject having or at risk of developing a disease or disorder associated with aberrant or unwanted 47153 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 47153 expression or activity. For example, such methods can be used to determine whether a subject can be effectively treated with an agent for a cell disorder associated with aberrant or unwanted 47153 expression or activity.

The methods of the invention can also be used to detect genetic alterations in a 47153 gene, thereby determining if a subject with the altered gene is at risk for a disorder characterized by misregulation in 47153 protein activity or nucleic acid expression, such as a 47153-related disorder. In preferred embodiments, the methods include detecting, in a sample from the subject, the presence or absence of a genetic alteration characterized by at least one of an alteration affecting the integrity of a gene encoding a 47153-protein, or the mis-expression of the 47153 gene. For example, such genetic alterations can be detected by ascertaining the existence of at least one of 1) a deletion of one or more nucleotides from a 47153 gene; 2) an addition of one or more nucleotides to a 47153 gene; 3) a substitution of one or more nucleotides of a 47153 gene, 4) a chromosomal rearrangement of a 47153 gene; 5) an alteration in the level of a messenger RNA transcript of a 47153 gene, 6) aberrant modification of a 47153 gene, such as of the methylation pattern of the genomic DNA, 7) the presence of a non-wild type splicing pattern of a messenger RNA transcript of a 47153 gene, 8) a non-wild type level of a 47153-protein, 9) allelic loss of a 47153 gene, and 10) inappropriate post-translational modification of a 47153-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 47153-gene. This method can include the steps of collecting a sample of cells from a subject, isolating nucleic acid (e.g., genomic, mRNA or both) from the sample, contacting the nucleic acid sample with one or more primers which specifically hybridize to a 47153 gene under conditions such that hybridization and amplification of the 47153 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 47153 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 47153 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 47153 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 47153 gene and detect mutations by comparing the sequence of the sample 47153 with the corresponding wild-type (control) sequence. Automated sequencing procedures can be utilized when performing the diagnostic assays (Naeve C. W. et al. (1995) *Biotechniques* 19:448–53), including sequencing by mass spectrometry.

Other methods for detecting mutations in the 47153 gene include methods in which protection from cleavage agents is used to detect mismatched bases in RNAIRNA or RNA/DNA heteroduplexes (Myers et al. (1985) *Science* 230:1242; Cotton et al. (1988) *Proc. Natl. Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 47153 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 47153 genes. For example, single strand conformation polymorphism (SSCP) can be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 47153 nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl. Acad. Sci USA* 86:6230).

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification can also be performed using Taq ligase for amplification (Barany (1991) *Proc. Natl. Acad. Sci USA* 88:189–93). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a 47153 gene.

Use of 47153 Molecules as Surrogate Markers

The 47153 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 47153 molecules of the invention can be detected, and can be correlated with one or more biological states in vivo. For example, the 47153 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 47153 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 47153 marker) transcription or expression, the amplified marker can be in a quantity which is more readily detectable than the drug itself. Also, the marker can be more easily detected due to the nature of the marker itself; for example, using the methods described herein, anti-47153 antibodies can be employed in an immune-based detection system for a 47153 protein marker, or 47153-specific radiolabeled probes can be used to detect a 47153 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am. J. Health-Syst. Pharm.* 56 Suppl. 3: S16–S20.

The 47153 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 47153 protein or RNA) for specific tumor markers in a subject, a drug or course of treatment can be selected that is optimized for the treatment of the specific tumor likely to be present in the subject. Similarly, the presence or absence of a specific sequence mutation in 47153 DNA can correlate with a 47153 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-47153 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent can, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety can be a protein or polypeptide possessing a desired biological activity. Such proteins can include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment:

The present invention provides for both prophylactic and therapeutic methods of treating a subject at risk of (or susceptible to) a disorder or having a disorder associated with aberrant or unwanted 47153 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 47153 molecules of the present invention or 47153 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 47153 expression or activity, by administering to the subject a 47153 or an agent which modulates 47153 expression or at least one 47153 activity. Subjects at risk for a disease which is caused or contributed to by aberrant or unwanted 47153 expression or activity can be identified by, for example, any or a combination of diagnostic or prognostic assays as described herein. Administration of a prophylactic agent can occur prior to the manifestation of symptoms characteristic of the 47153 aberrance, such that a disease or disorder is prevented or, alternatively, delayed in its progression. Depending on the type of 47153 aberrance, for example, a 47153, 47153 agonist or 47153 antagonist agent can be used for treating the subject. The appropriate agent can be determined based on screening assays described herein.

It is possible that some 47153 disorders can be caused, at least in part, by an abnormal level of gene product, or by the presence of a gene product exhibiting abnormal activity. As such, the reduction in the level and/or activity of such gene products would bring about the amelioration of disorder symptoms.

The 47153 molecules can act as novel diagnostic targets and therapeutic agents for controlling one or more of cellular proliferative and/or differentiative disorders, disorders associated with bone metabolism, immune, e.g., inflammatory, disorders, cardiovascular disorders, including endothelial cell disorders, liver disorders, viral diseases, pain or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states maybe categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The 47153 molecules of the invention can be used to monitor, treat and/or diagnose a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol/Hemotol. 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Aberrant expression and/or activity of 47153 molecules can mediate disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities mediated by 47153 molecules effects in bone cells, e.g. osteoclasts and osteoblasts, that can in turn result in bone formation and degeneration. For example, 47153 molecules can support different activities of bone resorbing osteoclasts such as the stimulation of differentiation of monocytes and mononuclear phagocytes into osteoclasts. Accordingly, 47153 molecules that modulate the production of bone cells can influence bone formation and degeneration, and thus can be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The 47153 nucleic acid and protein of the invention can be used to treat and/or diagnose a variety of immune, e.g., inflammatory (e.g. respiratory inflammatory) disorders. Examples immune and inflammatory disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, inflammatory bowel disease, e.g. Crohn's disease and ulcerative colitis, aphthous ulcer, iritis, conjunctivitis, keratoconjunctivitis, asthma, allergic asthma, chronic obstructive pulmonary disease, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, atrial fibrillation, long-QT syndrome, congestive heart failure, sinus node dysfunction, angina, heart failure, hypertension, atrial fibrillation, atrial flutter, cardiomyopathiues, e.g., dilated cardiomyopathy or idiopathic cardiomyopathy, myocardial infarction, coronary artery disease, coronary artery spasm, ischemic disease, arrhythmia, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovasular disease or disorder also includes an endothelial cell disorder.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein can be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 47153 molecules can play an important role in the etiology of certain viral diseases, including but not limited to Hepatitis B, Hepatitis C and Herpes Simplex Virus (HSV). Modulators of 47153 activity could be used to control viral diseases. The modulators can be used in the treatment and/or diagnosis of viral infected tissue or virus-associated tissue fibrosis, especially liver and liver fibrosis. Also, 47153 modulators can be used in the treatment and/or diagnosis of virus-associated carcinoma, especially hepatocellular cancer.

Additionally, 47153 can play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g. joint pain; tooth pain; headaches; pain associated with surgery; pain related to irritable bowel syndrome; or chest pain.

As discussed, successful treatment of 47153 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 47153 disorders. Such molecules can include, but are not limited to peptides, phosphopeptides, small organic or inorganic molecules, or antibodies (including, for example, polyclonal, monoclonal, humanized, human, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 47153 expression is through the use of aptamer molecules specific for 47153 protein. Aptamers are nucleic acid molecules having a tertiary structure which permits them to specifically or selectively bind to protein ligands (see, e.g., Osborne, et al. (1997) *Curr. Opin. Chem Biol.* 1: 5–9; and Patel, D. J. (1997) *Curr Opin Chem Biol* 1:32–46). Since nucleic acid molecules can in many cases be more conveniently introduced into target cells than therapeutic protein molecules can be, aptamers offer a method by which 47153 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of 47153 disorders. For a description of antibodies, see the Antibody section above.

In circumstances wherein injection of an animal or a human subject with a 47153 protein or epitope for stimulating antibody production is harmful to the subject, it is possible to generate an immune response against 47153 through the use of anti-idiotypic antibodies (see, for example, Herlyn, D. (1999) *Ann Med* 31:66–78; and Bbattacharya-Chattejee, M., and Foon, K. A. (1998) *Cancer Treat Res.* 94:51–68). If an anti-idiotypic antibody is introduced into a mammal or human subject, it should stimulate the production of anti-anti-idiotypic antibodies, which should be specific to the 47153 protein. Vaccines directed to a disease characterized by 47153 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g. Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate 47153 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 47153 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of 47153 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142–2144.

Another aspect of the invention pertains to methods of modulating 47153 expression or activity for therapeutic purposes. Accordingly, in an exemplary embodiment, the modulatory method of the invention involves contacting a cell with a 47153 or agent that modulates one or more of the activities of 47153 protein activity associated with the cell. An agent that modulates 47153 protein activity can be an agent as described herein, such as a nucleic acid or a protein, a naturally-occurring target molecule of a 47153 protein (e.g., a 47153 substrate or receptor), a 47153 antibody, a 47153 agonist or antagonist, a peptidomimetic of a 47153 agonist or antagonist, or other small molecule.

In one embodiment, the agent stimulates one or 47153 activities. Examples of such stimulatory agents include active 47153 protein and a nucleic acid molecule encoding 47153. In another embodiment, the agent inhibits one or more 47153 activities. Examples of such inhibitory agents include antisense 47153 nucleic acid molecules, anti-47153 antibodies, and 47153 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 47153 protein or nucleic acid molecule. In one embodiment, the method involves administering an agent (e.g., an agent identified by a screening assay described herein), or combination of agents that modulates (e.g., up regulates or down regulates) 47153 expression or activity. In another embodiment, the method involves administering a 47153 protein or nucleic acid molecule as therapy to compensate for reduced, aberrant, or unwanted 47153 expression or activity.

Stimulation of 47153 activity is desirable in situations in which 47153 is abnormally downregulated and/or in which increased 47153 activity is likely to have a beneficial effect. For example, stimulation of 47153 activity is desirable in situations in which a 47153 is downregulated and/or in which increased 47153 activity is likely to have a beneficial effect. Likewise, inhibition of 47153 activity is desirable in situations in which 47153 is abnormally upregulated and/or in which decreased 47153 activity is likely to have a beneficial effect.

Pharmacogenonics

The 47153 molecules of the present invention, as well as agents, or modulators which have a stimulatory or inhibitory effect on 47153 activity (e.g., 47153 gene expression) as identified by a screening assay described herein can be administered to individuals to treat (prophylactically or therapeutically) 47153-associated disorders (e.g., aberrant or deficient activity associated with catalyzing the synthesis of glycoconjugates function) associated with aberrant or unwanted 47153 activity. In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 47153 molecule or 47153 modulator as well as tailoring the dosage and/or therapeutic regimen of treatment with a 47153 molecule or 47153 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983–985 and Linder, M. W. et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP can occur once per every 1000 bases of DNA. A SNP can be involved in a disease process, however, the vast majority can not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach", can be utilized to identify genes that predict drug response. According to this method, if a gene that encodes a drug's target is known (e.g., a 47153 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 47153 molecule or 47153 modulator of the present invention) can give an indication whether gene pathways related to toxicity have been turned on.

In formation generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 47153 molecule or 47153 modulator, such as a modulator identified by one of the exemplary screening assays described herein.

The present invention further provides methods for identifying new agents, or combinations, that are based on identifying agents that modulate the activity of one or more of the gene products encoded by one or more of the 47153 genes of the present invention, wherein these products can be associated with resistance of the cells to a therapeutic agent. Specifically, the activity of the proteins encoded by the 47153 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 47153 protein can be applied in clinical trials. For example, the effectiveness of an agent determined by a screening assay as described herein to increase 47153 gene expression, protein levels, or upregulate 47153 activity, can be monitored in clinical trials of subjects exhibiting decreased 47153 gene expression, protein levels, or downregulated 47153 activity. Alternatively, the effectiveness of an agent determined by a screening assay to decrease 47153 gene expression, protein levels, or downregulate 47153 activity, can be monitored in clinical trials of subjects exhibiting increased 47153 gene expression, protein levels, or upregulated 47153 activity. In such clinical trials, the expression or activity of a 47153 gene, and preferably, other genes that have been implicated in, for example, a glycosyltransferase-associated or another 47153-associated disorder can be used as a "read out" or markers of the phenotype of a particular cell.

Other Embodiments

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses 47153 or from a cell or subject in which a 47153 mediated response has been elicited; contacting the array with a 47153 nucleic acid (preferably purified), a 47153 polypeptide (preferably purified), or an anti-47153 antibody, and thereby evaluating the plurality of capture probes. Binding, e.g., in the case of a nucleic acid, hybridization with a capture probe at an address of the plurality, is detected, e.g., by a signal generated from a label attached to the 47153 nucleic acid, polypeptide, or antibody.

The capture probes can be a set of nucleic acids from a selected sample, e.g., a sample of nucleic acids derived from a control or non-stimulated tissue or cell.

The method can include contacting the 47153 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 47153. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing 47153, e.g., analyzing structure, function, or relatedness to other nucleic acid or amino acid sequences. The method includes: providing a 47153 nucleic acid or amino acid sequence; comparing the 47153 sequence with one or more preferably a plurality of sequences from a collection of sequences, e.g., a nucleic acid or protein sequence database; to thereby analyze 47153.

The method can include evaluating the sequence identity between a 47153 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of 47153. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotide which hybridizes to one allele provides a signal that is distinguishable from an oligonucleotides which hybridizes to a second allele.

The sequences of 47153 molecules are provided in a variety of mediums to facilitate use thereof. A sequence can be provided as a manufacture, other than an isolated nucleic acid or amino acid molecule, which contains a 47153 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exist in nature or in purified form.

A 47153 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon 47153 sequence information of the present invention.

As used herein, the term "electronic apparatus" is intended to include any suitable computing or processing apparatus of other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 47153 sequence information.

A variety of data storage structures are available to a skilled artisan for creating a computer readable medium having recorded thereon a 47153 nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the 47153 nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

The present invention therefore provides a medium for holding instructions for performing a method for determining whether a subject has a glycosyltransferase-associated or another 47153-associated disease or disorder or a predisposition to a glycosyltransferase-associated or another 47153-associated disease or disorder, wherein the method comprises the steps of determining 47153 sequence information associated with the subject and based on the 47153 sequence information, determining whether the subject has a glycosyltransferase-associated or another 47153-associated disease or disorder and/or recommending a particular treatment for the disease, disorder, or pre-disease condition.

The present invention further provides in an electronic system and/or in a network, a method for determining whether a subject has a glycosyltransferase-associated or another 47153-associated disease or disorder or a pre-disposition to a disease associated with 47153, wherein the method comprises the steps of determining 47153 sequence information associated with the subject, and based on the 47153 sequence information, determining whether the subject has a glycosyltransferase-associated or another 47153-associated disease or disorder or a pre-disposition to a glycosyltransferase-associated or another 47153-associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a glycosyltransferase-associated or another 47153-associated disease or disorder or a pre-disposition to a glycosyltransferase-associated or another 47153-associated disease or disorder, said method comprising the steps of receiving 47153 sequence information from the subject and/or information related thereto, receiving phenotypic information associated with the subject, acquiring information from the network corresponding to 47153 and/or corresponding to a glycosyltransferase-associated or another 47153-associated disease or disorder, and based on one or more of the phenotypic information, the 47153 information (e.g., sequence information and/or information related thereto), and the acquired information, determining whether the subject has a glycosyltransferase-associated or another 47153-associated disease or disorder or a pre-disposition to a glycosyltransferase-associated or another 47153-associated disease or disorder. The method may further comprise the step of recommending a particular treatment for the disease, disorder, or pre-disease condition.

The present invention also provides a business method for determining whether a subject has a glycosyltransferase-associated or another 47153-associated disease or disorder or a pre-disposition to a glycosyltransferase-associated or another 47153-associated disease or disorder, said method comprising the steps of receiving information related to 47153 (e.g., sequence information and/or information related thereto), receiving phenotypic information associated with the subject, acquiring information from the network related to 47153 and/or related to a glycosyltransferase-associated or another 47153-associated disease or disorder, and based on one or more of the phenotypic information, the 47153 information, and the acquired information, determining whether the subject has a glycosyltransferase-associated or another 47153-associated disease or disorder or a predisposition to a glycosyltransferase-associated or another 47153-associated disease or disorder. The method may further comprise the step of recommending a particular treatment for the disease, disorder, or pre-disease condition.

The invention also includes an array comprising a 47153 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be 47153. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell—cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a glycosyltransferase-associated or another 47153-associated disease or disorder, progression of glycosyltransferase-associated or another 47153-associated disease or disorder, and processes, such a cellular transformation associated with the glycosyltransferase-associated or another 47153-associated disease or disorder.

The array is also useful for ascertaining the effect of the expression of a gene on the expression of other genes in the same cell or in different cells (e.g., ascertaining the effect of 47153 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 47153) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 47153 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 47153 sequence, or record, in computer readable form; comparing a second sequence to the 47153 sequence; thereby analyzing a sequence. Comparison can include comparing to sequences for sequence identity or determining if one sequence is included within the other, e.g., determining if the 47153 sequence includes a sequence being compared. In a preferred embodiment the 47153 or second sequence is stored on a first computer, e.g., at a first site and the comparison is performed, read, or recorded on a second computer, e.g., at a second site. E.g., the 47153 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

The contents of all references, patents and published patent applications cited throughout this application are incorporated herein by reference.

EXAMPLES

Example 1

Identification and Characterization of Human 47153 cDNAs

The human 47153 sequence (FIGS. 1A–B; SEQ ID NO:1), which is approximately 1788 nucleotides long including untranslated regions, contain predicted methionine-initiated coding sequences of about 1332 nucleotides (nucleotides 313–1644 of SEQ ID NO:1, SEQ ID NO:3). The coding sequence encodes a 443 amino acid protein (SEQ ID NO:2).

Example 2

Tissue Distribution of 47153 mRNA

Northern blot hybridizations with various RNA samples can be performed under standard conditions and washed under stringent conditions, i.e., 0.2×SSC at 65° C. A DNA probe corresponding to all or a portion of the 47153 cDNA (SEQ ID NO:1) or 47153 cDNA can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 3

Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Human 47153 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 47153 gene. Each human 47153 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forvard and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 47153 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 47153 gene is normalized by subtracting the Ct value of the β-2 microglobulin gene to obtain a ΔCt value using the following formula: $\Delta Ct = Ct_{human\ 47153} - Ct_{\beta-2\ microglobulin}$. Expression is then calibrated against a cDNA sample showing a comparatively low level of expression of the human 47153 gene. The ΔCt value for the calibrator sample is then subtracted from ΔCt for each tissue sample according to the following formula: $\Delta\Delta Ct = \Delta Ct_{sample} - \Delta Ct_{calibrator}$. Relative expression is then calculated using the arithmetic formula given by 2-ΔΔCt. Expression of the target human 47153 gene in each of the tissues tested is then graphically represented as discussed in more detail below.

TaqMan real-time quantitative RT-PCR is used to detect the presence of RNA transcript corresponding to human 47153 relative to a no template control in a panel of human tissues or cells.

Taqman results on the phase I tissue panel showed highest expression of 47153 orthologs in the normal brain cortex as shown in the following Table 1.

TABLE 1

Phase 1.6.5 Expression of 47153 W/β2

| Tissue Type | Mean | β 2 Mean | ∂∂ Ct | Expression |
|---|---|---|---|---|
| Artery normal | 40 | 21.82 | 18.18 | 0 |
| Aorta diseased | 40 | 22.22 | 17.79 | 0 |
| Vein normal | 40 | 19.71 | 20.29 | 0 |
| Coronary SMC | 40 | 20.4 | 19.6 | 0 |
| HUVEC | 40 | 20.61 | 19.4 | 0 |
| Hemangloma | 40 | 19.32 | 20.68 | 0 |
| Heart normal | 40 | 20.48 | 19.52 | 0 |
| Heart CHF | 40 | 20.45 | 19.55 | 0 |
| Kidney | 40 | 20.06 | 19.95 | 0 |
| Skeletal Muscle | 40 | 21.73 | 18.27 | 0 |
| Adipose normal | 40 | 20.3 | 19.7 | 0 |
| Pancreas | 40 | 21.98 | 18.02 | 0 |
| primary osteoblasts | 40 | 20.09 | 19.91 | 0 |
| Osteoclasts (diff) | 40 | 17.32 | 22.68 | 0 |
| Skin normal | 40 | 22.02 | 17.98 | 0 |
| Spinal cord normal | 40 | 20.42 | 19.58 | 0 |
| Brain Cortex normal | 28.9 | 21.52 | 7.38 | 6.0243 |
| Brain Hypothalamus normal | 39.39 | 21.86 | 17.54 | 0 |
| Nerve | 40 | 21.56 | 18.45 | 0 |
| DRG (Dorsal Root Ganglion) | 40 | 20.91 | 19.09 | 0 |
| Breast normal | 40 | 20.36 | 19.64 | 0 |
| Breast tumor | 40 | 20.29 | 19.71 | 0 |
| Ovary normal | 40 | 19.48 | 20.52 | 0 |
| Ovary Tumor | 40 | 18.37 | 21.63 | 0 |
| Prostate Normal | 40 | 19.27 | 20.73 | 0 |
| Prostate Tumor | 39.67 | 20.07 | 19.61 | 0 |
| Salivary glands | 40 | 19.33 | 20.67 | 0 |
| Colon normal | 40 | 18.34 | 21.66 | 0 |
| Colon Tumor | 40 | 20.92 | 19.08 | 0 |
| Lung normal | 40 | 18.3 | 21.7 | 0 |
| Lung tumor | 40 | 20.26 | 19.74 | 0 |
| Lung COPO | 40 | 20.29 | 19.71 | 0 |
| Colon IBD | 40 | 18.31 | 21.69 | 0 |
| Liver normal | 40 | 19.73 | 20.27 | 0 |
| Liver fibrosis | 40 | 20.48 | 19.52 | 0 |
| Spleen normal | 40 | 18.46 | 21.54 | 0 |
| Tonsil normal | 40 | 18.18 | 21.82 | 0 |
| Lymph node normal | 40 | 19.75 | 20.25 | 0 |
| Small intestine normal | 40 | 19.84 | 20.16 | 0 |
| Macrophages | 40 | 16.75 | 23.25 | 0 |
| Synovium | 40 | 19.57 | 20.43 | 0 |
| BM-MNC | 40 | 18.93 | 21.07 | 0 |
| Activated PBMC | 40 | 17.74 | 22.26 | 0 |
| Neutrophils | 40 | 17.84 | 22.16 | 0 |
| Megakaryocytes | 40 | 18.81 | 21.2 | 0 |
| Erythroid | 40 | 20.86 | 19.14 | 0 |
| positive control | 26.09 | 20.02 | 6.08 | 14.8335 |

As seen by these results, 47153 molecules have been found to be expressed in brain tissue. As such, these molecules are useful for treating brain disorders where 47153 molecules are underexpressed or overexpressed. Therefore, activators or inhibitors of the 47153 molecules are useful for the treatment of brain disorders, and useful as a diagnostic.

Example 4

Recombinant Expression of 47153 in Bacterial Cells

In this example, 47153 is expressed as a recombinant glutathione-S-transferase (GST) fusion polypeptide in *E. coli* and the fusion polypeptide is isolated and characterized. Specifically, 47153 is fused to GST and this fusion polypeptide is expressed in *E. coli*, e.g., strain PEB199. Expression of the GST47153 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 5

Expression of Recombinant 47153 Protein in COS Cells

To express the 47153 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 47153 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 47153 DNA sequence is amplified by PCR using two primers. The 5' primer contains the restriction site of interest followed by approximately twenty nucleotides of the 47153 coding sequence starting from the initiation codon; the 3' end sequence contains complementary sequences to the other restriction site of interest, a translation stop codon, the HA tag or FLAG tag and the last 20 nucleotides of the 47153 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 47153 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 47153-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning*: A Laboratory ManuaL 2nd, ed., Cold Spring Harbor Laboratory, Cold Spring Harbor Laboratory Press, Cold Spring Harbor, N.Y., 1989. The expression of the 47153 polypeptide is detected by radiolabelling ($^{35}$S-methionine or $^{35}$S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 47153 coding sequence is cloned directly into the polylinker of the pcDNA/Amp vector using the appropriate restriction sites. The resulting plasmid is transfected into COS cells in the manner described above, and the expression of the 47153 polypeptide is detected by radiolabelling and immunoprecipitation using a 47153 specific monoclonal antibody.

Equivalents

Those skilled in the art will recognize, or be able to ascertain using no more than routine experimentation, many equivalents to the specific embodiments of the invention described herein.

---

What is claimed is:

1. An isolated nucleic acid molecule comprising the nucleotide sequence SEQ ID NO:1 or SEQ ID NO:3.

2. A recombinant host cell which contains the nucleic acid of claim 1.

3. The nucleic acid molecule of claim 1, further comprising nucleic acid sequences encoding a heterologous polypeptide.

4. The host cell of claim 2 which is a mammalian host cell.

5. A recombinant non-human mammalian host cell containing the nucleic acid molecule of claim 1.

6. A method for producing a polypeptide, comprising culturing the host cell of claim 2 under conditions in which the polypeptide is expressed.

7. An isolated nucleic acid molecule which encodes a polypeptide comprising the amino acid sequence of SEQ ID NO:2.

8. A recombinant host cell which contains the nucleic acid of claim 7.

9. The host cell of claim 8 which is a mammalian host cell.

10. A recombinant non-human mammalian host cell containing the nucleic acid molecule of claim 7.

11. A method for producing a polypeptide, comprising culturing the host cell of claim 8 under conditions in which the polypeptide is expressed.

* * * * *

SEQUENCE LISTING

<160> NUMBER OF SEQ ID NOS: 14

<210> SEQ ID NO 1
<211> LENGTH: 1788
<212> TYPE: DNA
<213> ORGANISM: Homo Sapiens
<220> FEATURE:
<221> NAME/KEY: CDS
<222> LOCATION: (314)...(1645)

<400> SEQUENCE: 1

```
agcggagctc aaccaggtat ctgcttggaa cccagccacc ataaagcctg ctagctaaaa      60
aaaawtttta catctctcag ttcattcggc acagacccct gcctcattca cctgtgactc     120
tgcttggaaa attcatcagt tacaaagcag ccaatgcaat tatctcaagg cattgaattc     180
tgcatctttt agtgaagaaa ataactgaac atggttttct tctgaagaca caaagtccaa     240
aggccaatca cacacctctt acatcgatct cttggaaatt gaaaaatgga cctttgaaaa     300
tgctagattt aca atg aga aat gcc ata att caa ggt tta ttc tat ggg        349
            Met Arg Asn Ala Ile Ile Gln Gly Leu Phe Tyr Gly
              1               5                  10 tcc ttg aca ttt ggg atc tgg aca gct ctg tta ttc ata tat ttg cac      397
Ser Leu Thr Phe Gly Ile Trp Thr Ala Leu Leu Phe Ile Tyr Leu His
         15                  20                  25 cat aat cat gtg agc agc tgg cag aag aaa agc cag gag cct ctg tca      445
His Asn His Val Ser Ser Trp Gln Lys Lys Ser Gln Glu Pro Leu Ser
 30                  35                  40 gct tgg tcc cct gga aaa aaa gtg cat cag caa att atc tat ggc tca      493
Ala Trp Ser Pro Gly Lys Lys Val His Gln Gln Ile Ile Tyr Gly Ser
 45                  50                  55                  60 gag caa ata cca aaa cct cat gta ata gtc aaa agg act gat gaa gat      541
Glu Gln Ile Pro Lys Pro His Val Ile Val Lys Arg Thr Asp Glu Asp
                 65                  70                  75 aaa gca aag tct atg tta ggt aca gat ttt aac cat aca aac cca gaa      589
Lys Ala Lys Ser Met Leu Gly Thr Asp Phe Asn His Thr Asn Pro Glu
             80                  85                  90 ctt cat aaa gaa ctt tta aaa tat gga ttt aat gtg att atc agt aga      637
Leu His Lys Glu Leu Leu Lys Tyr Gly Phe Asn Val Ile Ile Ser Arg
         95                 100                 105 agc ttg ggc atc gaa aga gaa gtg cca gat acc agg agt aaa atg cgt      685
Ser Leu Gly Ile Glu Arg Glu Val Pro Asp Thr Arg Ser Lys Met Arg
110                 115                 120 ctt caa aaa cat tac cca gcc cgc ctc ccg act gcc agc att gtc att      733
Leu Gln Lys His Tyr Pro Ala Arg Leu Pro Thr Ala Ser Ile Val Ile
125                 130                 135                 140 tgc ttc tat aat gaa gaa tgt aat gcc ttg ttt cag acc atg tcc agt      781
Cys Phe Tyr Asn Glu Glu Cys Asn Ala Leu Phe Gln Thr Met Ser Ser
                145                 150                 155 gtc acg aac ctc acg cca cac tat ttt ctt gaa gaa att att ttg gta      829
Val Thr Asn Leu Thr Pro His Tyr Phe Leu Glu Glu Ile Ile Leu Val
            160                 165                 170
```

```
gat gac atg agc aaa gtt gat gat ttg aaa gaa aaa cta gac tat cac      877
Asp Asp Met Ser Lys Val Asp Asp Leu Lys Glu Lys Leu Asp Tyr His
            175                 180                 185 ctg gaa act ttt cgg gga aag gtt aaa ata ata aga aac aaa aag aga      925
Leu Glu Thr Phe Arg Gly Lys Val Lys Ile Ile Arg Asn Lys Lys Arg
        190                 195                 200 gag ggg ctg att cga gca agg ctg att gga gct tct cat gct tca ggg      973
Glu Gly Leu Ile Arg Ala Arg Leu Ile Gly Ala Ser His Ala Ser Gly
205                 210                 215                 220 gat gtt ctg gtg ttc ctg gac agc cac tgt gag gtg aac aga gta tgg     1021
Asp Val Leu Val Phe Leu Asp Ser His Cys Glu Val Asn Arg Val Trp
                225                 230                 235 ctg gag ccc ctg ctg cat gcc att gcc aag gac ccc aaa atg gtg gtg     1069
Leu Glu Pro Leu Leu His Ala Ile Ala Lys Asp Pro Lys Met Val Val
            240                 245                 250 tgc ccc ctg ata gat gtc att gat gat aga act ctg gag tat aag ccc     1117
Cys Pro Leu Ile Asp Val Ile Asp Asp Arg Thr Leu Glu Tyr Lys Pro
        255                 260                 265 tct cct ctt gta agg gga act ttt gat tgg aac cta caa ttt aaa tgg     1165
Ser Pro Leu Val Arg Gly Thr Phe Asp Trp Asn Leu Gln Phe Lys Trp
270                 275                 280 gat aat gtt ttc tct tat gag atg gat gga cca gaa gga tct act aaa     1213
Asp Asn Val Phe Ser Tyr Glu Met Asp Gly Pro Glu Gly Ser Thr Lys
285                 290                 295                 300 cca atc cgg tca cct gca atg tct gga gga att ttt gct ata cgt cgg     1261
Pro Ile Arg Ser Pro Ala Met Ser Gly Gly Ile Phe Ala Ile Arg Arg
                305                 310                 315 cat tat ttt aat gaa att gga cag tat gac aag gat atg gat ttt tgg     1309
His Tyr Phe Asn Glu Ile Gly Gln Tyr Asp Lys Asp Met Asp Phe Trp
            320                 325                 330 gga aga gaa aat ttg gaa ctt tca cta agg atc tgg atg tgt gga ggc     1357
Gly Arg Glu Asn Leu Glu Leu Ser Leu Arg Ile Trp Met Cys Gly Gly
        335                 340                 345 caa ctc ttt ata atc ccc tgc tct cga gta gga cat atc agt aag aaa     1405
Gln Leu Phe Ile Ile Pro Cys Ser Arg Val Gly His Ile Ser Lys Lys
350                 355                 360 caa act gga aaa cct tct aca atc atc agt gct atg aca cat aac tac     1453
Gln Thr Gly Lys Pro Ser Thr Ile Ile Ser Ala Met Thr His Asn Tyr
365                 370                 375                 380 cta aga ctg gtg cac gtt tgg ctg gat gaa tat aag gag cag ttt ttt     1501
Leu Arg Leu Val His Val Trp Leu Asp Glu Tyr Lys Glu Gln Phe Phe
                385                 390                 395 ctt cga aag cct ggt ctg aaa tat gtc acc tac gga aat att cgc gag     1549
Leu Arg Lys Pro Gly Leu Lys Tyr Val Thr Tyr Gly Asn Ile Arg Glu
            400                 405                 410 cgt gtt gag tta agg aaa cga ctg ggt gca aag tca ttt cag tgg tat     1597
Arg Val Glu Leu Arg Lys Arg Leu Gly Cys Lys Ser Phe Gln Trp Tyr
        415                 420                 425 ttg gat aat gtc ttc cca gag ttg gag gca tct gtg aac agc ctg tga    1645
Leu Asp Asn Val Phe Pro Glu Leu Glu Ala Ser Val Asn Ser Leu *
430                 435                 440 aaggaaaaca aatcactttc attaataaag ggttaaaagt ctcctagtca ttcaacatag   1705
tgtcacaaga gtgtaagttt ggaacatcgt ggaattacgt gaaatgcaat taaaaaaata   1765
tgaccagaaa aaaaaaaaaa aaa                                          1788

<210> SEQ ID NO 2
<211> LENGTH: 443
<212> TYPE: PRT
<213> ORGANISM: Homo Sapiens
```

<400> SEQUENCE: 2

```
Met Arg Asn Ala Ile Ile Gln Gly Leu Phe Tyr Gly Ser Leu Thr Phe
 1               5                  10                  15
Gly Ile Trp Thr Ala Leu Leu Phe Ile Tyr Leu His His Asn His Val
                20                  25                  30
Ser Ser Trp Gln Lys Lys Ser Gln Glu Pro Leu Ser Ala Trp Ser Pro
            35                  40                  45
Gly Lys Lys Val His Gln Gln Ile Ile Tyr Gly Ser Glu Gln Ile Pro
        50                  55                  60
Lys Pro His Val Ile Val Lys Arg Thr Asp Glu Asp Lys Ala Lys Ser
65                  70                  75                  80
Met Leu Gly Thr Asp Phe Asn His Thr Asn Pro Glu Leu His Lys Glu
                85                  90                  95
Leu Leu Lys Tyr Gly Phe Asn Val Ile Ile Ser Arg Ser Leu Gly Ile
            100                 105                 110
Glu Arg Glu Val Pro Asp Thr Arg Ser Lys Met Arg Leu Gln Lys His
        115                 120                 125
Tyr Pro Ala Arg Leu Pro Thr Ala Ser Ile Val Ile Cys Phe Tyr Asn
    130                 135                 140
Glu Glu Cys Asn Ala Leu Phe Gln Thr Met Ser Ser Val Thr Asn Leu
145                 150                 155                 160
Thr Pro His Tyr Phe Leu Glu Glu Ile Ile Leu Val Asp Asp Met Ser
                165                 170                 175
Lys Val Asp Asp Leu Lys Glu Lys Leu Asp Tyr His Leu Glu Thr Phe
            180                 185                 190
Arg Gly Lys Val Lys Ile Arg Asn Lys Lys Arg Glu Gly Leu Ile
        195                 200                 205
Arg Ala Arg Leu Ile Gly Ala Ser His Ala Ser Gly Asp Val Leu Val
    210                 215                 220
Phe Leu Asp Ser His Cys Glu Val Asn Arg Val Trp Leu Glu Pro Leu
225                 230                 235                 240
Leu His Ala Ile Ala Lys Asp Pro Lys Met Val Val Cys Pro Leu Ile
                245                 250                 255
Asp Val Ile Asp Asp Arg Thr Leu Glu Tyr Lys Pro Ser Pro Leu Val
            260                 265                 270
Arg Gly Thr Phe Asp Trp Asn Leu Gln Phe Lys Trp Asp Asn Val Phe
        275                 280                 285
Ser Tyr Glu Met Asp Gly Pro Glu Gly Ser Thr Lys Pro Ile Arg Ser
    290                 295                 300
Pro Ala Met Ser Gly Gly Ile Phe Ala Ile Arg Arg His Tyr Phe Asn
305                 310                 315                 320
Glu Ile Gly Gln Tyr Asp Lys Asp Met Asp Phe Trp Gly Arg Glu Asn
                325                 330                 335
Leu Glu Leu Ser Leu Arg Ile Trp Met Cys Gly Gly Gln Leu Phe Ile
            340                 345                 350
Ile Pro Cys Ser Arg Val Gly His Ile Ser Lys Lys Gln Thr Gly Lys
        355                 360                 365
Pro Ser Thr Ile Ile Ser Ala Met Thr His Asn Tyr Leu Arg Leu Val
    370                 375                 380
His Val Trp Leu Asp Glu Tyr Lys Glu Gln Phe Phe Leu Arg Lys Pro
385                 390                 395                 400
Gly Leu Lys Tyr Val Thr Tyr Gly Asn Ile Arg Glu Arg Val Glu Leu
```

-continued

```
            405                 410                 415
Arg Lys Arg Leu Gly Cys Lys Ser Phe Gln Trp Tyr Leu Asp Asn Val
        420                 425                 430

Phe Pro Glu Leu Glu Ala Ser Val Asn Ser Leu
        435                 440
```

<210> SEQ ID NO 3
<211> LENGTH: 1329
<212> TYPE: DNA
<213> ORGANISM: Homo sapiens

<400> SEQUENCE: 3

```
atgagaaatg ccataattca aggtttattc tatgggtcct tgacatttgg gatctggaca      60
gctctgttat tcatatattt gcaccataat catgtgagca gctggcagaa gaaaagccag     120
gagcctctgt cagcttggtc ccctggaaaa aaagtgcatc agcaaattat ctatggctca     180
gagcaaatac caaaacctca tgtaatagtc aaaaggactg atgaagataa agcaaagtct     240
atgttaggta cagattttaa ccatacaaac ccagaacttc ataaagaact tttaaaatat     300
ggatttaatg tgattatcag tagaagcttg ggcatcgaaa gagaagtgcc agataccagg     360
agtaaaatgc gtcttcaaaa acattaccca gcccgcctcc cgactgccag cattgtcatt     420
tgcttctata tgaagaatg taatgccttg tttcagacca tgtccagtgt cacgaacctc     480
acgccacact attttcttga agaaattatt ttggtagatg acatgagcaa agttgatgat     540
ttgaaagaaa aactagacta tcacctggaa acttttcggg aaaggttaa aataataaga     600
aacaaaaaga gagagggggct gattcgagca aggctgattg gagcttctca tgcttcaggg     660
gatgttctgg tgttcctgga cagccactgt gaggtgaaca gagtatggct ggagcccctg     720
ctgcatgcca ttgccaagga ccccaaaatg gtggtgtgcc ccctgataga tgtcattgat     780
gatagaactc tggagtataa gccctctcct cttgtaaggg gaacttttga ttggaaccta     840
caatttaaat gggataatgt tttctcttat gagatggatg accagaaagg atctactaaa     900
ccaatccggt cacctgcaat gtctggagga atttttgcta tcgtcggca ttattttaat     960
gaaattggac agtatgacaa ggatatggat ttttggggaa gagaaaattt ggaactttca    1020
ctaaggatct ggatgtgtgg aggccaactc tttataatcc cctgctctcg agtaggacat    1080
atcagtaaga aacaaactgg aaaaccttct acaatcatca gtgctatgac acataactac    1140
ctaagactgg tgcacgtttg gctggatgaa tataaggagc agttttttct tcgaaagcct    1200
ggtctgaaat atgtcaccta cggaaatatt cgcgagcgtg ttgagttaag gaaacgactg    1260
ggttgcaagt catttcagtg gtatttggat aatgtcttcc cagagttgga ggcatctgtg    1320
aacagcctg                                                            1329
```

<210> SEQ ID NO 4
<211> LENGTH: 150
<212> TYPE: PRT
<213> ORGANISM: Artificial Sequence
<220> FEATURE:
<223> OTHER INFORMATION: Consensus amino acid sequence

<400> SEQUENCE: 4

```
Ser Ile Ile Ile Pro Thr Tyr Asn Glu Glu Lys Tyr Leu Glu Glu Cys
 1               5                   10                  15

Leu Glu Ser Leu Leu Asn Gln Thr Thr Tyr Glu Asn Phe Glu Ile Ile
            20                  25                  30

Val Val Asp Asp Gly Ser Thr Asp Gly Thr Val Glu Ile Leu Glu Glu
```

```
                    35                  40                  45
Tyr Ala Lys Asp Pro Arg Ile Arg Val Ile Arg Leu Glu Glu Asn Leu
     50                  55                  60

Gly Leu Ala Ala Ala Arg Asn Ala Gly Leu Lys His Ala Thr Gly Asp
 65                  70                  75                  80

Tyr Asp Tyr Ile Ala Phe Leu Asp Ala Asp Glu Val Pro Asp Trp
                 85                  90                  95

Leu Glu Lys Leu Leu Glu Leu Leu Glu Lys Asn Gly Ala Asp Ile Val
                100                 105                 110

Ile Gly Arg Val Ile Asn Glu Asn Lys Gly Arg Leu Asn Gly Lys Leu
            115                 120                 125

Arg Leu Leu Val Phe Leu Ile Gly Ser Asn Ala Leu Tyr Arg Arg Glu
        130                 135                 140

Ala Leu Glu Lys Leu Leu
145                 150

<210> SEQ ID NO 5
<211> LENGTH: 142
<212> TYPE: PRT
<213> ORGANISM: Artificial Sequence
<220> FEATURE:
<223> OTHER INFORMATION: Consensus amino acid sequence

<400> SEQUENCE: 5

Thr Asp Pro Ile Arg Ser Pro Thr Met Ala Gly Gly Leu Phe Ala Ile
  1               5                  10                  15

Asn Lys Glu Tyr Phe Glu Leu Gly Thr Tyr Asp Pro Gly Met Asp
                 20                  25                  30

Ile Trp Gly Gly Glu Asn Leu Glu Leu Ser Phe Arg Val Trp Gln Gly
             35                  40                  45

Gly Arg Leu Glu Ile Val Pro Cys Ser His Val Gly His Val Phe Arg
 50                  55                  60

Lys Arg Ser Pro Tyr Thr Phe Pro Gly Lys Gly Ser Gly Lys Asp Val
 65                  70                  75                  80

Ile Ser Arg Asn Thr Val Arg Val Ala Glu Val Trp Met Asp Asp Tyr
                 85                  90                  95

Lys Glu Tyr Phe Tyr Lys His Asn Pro Gln Ala Arg Lys Val Arg Asp
                100                 105                 110

Phe Gly Asp Ile Ser Glu Arg Lys Glu Leu Arg Glu Lys Leu Gln Cys
            115                 120                 125

Lys Ser Phe Lys Trp Tyr Leu Glu Asn Val Tyr Pro Asp Leu
        130                 135                 140

<210> SEQ ID NO 6
<211> LENGTH: 164
<212> TYPE: PRT
<213> ORGANISM: Artificial Sequence
<220> FEATURE:
<223> OTHER INFORMATION: Consensus amino acid sequence

<400> SEQUENCE: 6

Ser Val Ser Val Ile Ile Pro Thr Tyr Asn Glu Glu Glu Ser Ile Leu
  1               5                  10                  15

Lys Thr Leu Val Ser Ser Val Leu Gln Gln Gln Tyr Glu Asn His Tyr
                 20                  25                  30

Glu Met Glu Glu Ile Ile Val Asp Asp Gly Ser Thr Asp Asn Thr
             35                  40                  45
```

```
Ala Glu Ile Val Glu Glu Tyr Ser Tyr Ser Ala Glu Lys Glu Ser Arg
 50                  55                  60

Val Lys Val Lys Val Ile Arg Asn Glu Lys Asn Ser Gly Met Ser Ser
 65                  70                  75                  80

Ala Met Asn Lys Gly Leu Lys His Ala Leu Ser Gly Ala Asp Gly Asp
             85                  90                  95

Ile Ile Asp Tyr Ile Val Phe Leu Asp Ser Asp Val His Met Ser
            100                 105                 110

Pro Asp Trp Leu Glu Lys Leu Ile Glu Ala Met Glu Glu Asp Asn Ala
            115                 120                 125

Asp Val Val Gly Ser Arg Gln Val Val Asn Asp Asn Lys Gln
    130                 135                 140

Tyr Ser Ser Ala Thr Arg Leu Ile Asn Met Glu Gly Gly Tyr Asn Trp
145                 150                 155                 160

Ser Met Met Tyr
```

<210> SEQ ID NO 7
<211> LENGTH: 116
<212> TYPE: PRT
<213> ORGANISM: Artificial Sequence
<220> FEATURE:
<223> OTHER INFORMATION: Consensus amino acid sequence

<400> SEQUENCE: 7

```
Lys Tyr Ala Phe Asn Ala Tyr Val Ser Asp Arg Ile Ser Leu Asn Arg
  1               5                  10                  15

Ser Ile Pro Asp Thr Arg His Pro Glu Cys Lys Asn Lys Lys Tyr Tyr
             20                  25                  30

Ser Asp Asn Leu Pro Thr Thr Ser Val Ile Ile Val Phe His Asn Glu
             35                  40                  45

Ala Trp Ser Thr Leu Leu Arg Thr Val His Ser Val Ile Asn Arg Thr
 50                  55                  60

Pro Pro His Leu Leu Lys Glu Ile Ile Leu Val Asp Asp Phe Ser Asp
 65                  70                  75                  80

Arg Pro His Leu Leu Lys Gln Lys Leu Glu Glu Tyr Val Lys Lys Lys
             85                  90                  95

Phe Pro Gly Lys Val Lys Ile Leu Arg Asn Glu Glu Arg Glu Gly Leu
            100                 105                 110

Ile Arg Ala Arg
            115
```

<210> SEQ ID NO 8
<211> LENGTH: 78
<212> TYPE: PRT
<213> ORGANISM: Artificial Sequence
<220> FEATURE:
<223> OTHER INFORMATION: Consensus amino acid sequence

<400> SEQUENCE: 8

```
Val Ile Asp Val Ile Asp Asp Asn Thr Phe Glu Tyr His Lys Ser Lys
  1               5                  10                  15

Ser Ser Asp Thr Ser Arg Gly Gly Phe Asp Trp Gly Leu His Phe Lys
             20                  25                  30

Trp His Pro Ile Pro Glu Glu Arg Lys Arg Lys Arg Arg Glu
             35                  40                  45

Asp Pro Thr Glu Pro Ile Arg Ser Pro Thr Met Ala Gly Gly Leu Phe
 50                  55                  60
```

```
Ala Ile Asp Arg Glu Tyr Phe Trp Glu Leu Gly Ser Tyr Asp
 65                  70                  75

<210> SEQ ID NO 9
<211> LENGTH: 62
<212> TYPE: PRT
<213> ORGANISM: Artificial Sequence
<220> FEATURE:
<223> OTHER INFORMATION: Consensus amino acid sequence

<400> SEQUENCE: 9

Met Asp Ile Trp Gly Gly Glu Asn Leu Glu Leu Ser Phe Arg Val Trp
  1               5                  10                  15

Gln Cys Gly Gly Lys Leu Glu Ile Val Pro Cys Ser Arg Val Gly His
                 20                  25                  30

Ile Phe Arg Lys Gln Ser Pro Tyr Thr Phe Pro Ser Gly Ser Ser Ser
             35                  40                  45

Asn Val Ile Ser Arg Asn Tyr Lys Arg Val Ala Glu Val Trp
         50                  55                  60

<210> SEQ ID NO 10
<211> LENGTH: 50
<212> TYPE: PRT
<213> ORGANISM: Artificial Sequence
<220> FEATURE:
<223> OTHER INFORMATION: Consensus amino acid sequence

<400> SEQUENCE: 10

Met Asp Glu Tyr Lys Glu Tyr Phe Tyr Lys Arg Arg Pro Asn Ala Tyr
  1               5                  10                  15

Arg Asn Val Asp Tyr Gly Asp Ile Ser Glu Arg Met Glu Leu Arg Glu
                 20                  25                  30

Lys Leu Gln Cys Lys Ser Phe Lys Trp Tyr Leu Glu Asn Val Tyr Pro
             35                  40                  45

Glu Leu
     50

<210> SEQ ID NO 11
<211> LENGTH: 43
<212> TYPE: PRT
<213> ORGANISM: Artificial Sequence
<220> FEATURE:
<223> OTHER INFORMATION: Consensus amino acid sequence

<400> SEQUENCE: 11

Leu Ile Gly Ala Lys Val Ala Thr Gly Glu Val Leu Thr Phe Leu Asp
  1               5                  10                  15

Ser His Cys Glu Cys Asn Glu Gly Trp Leu Gly Pro Leu Leu Glu Arg
                 20                  25                  30

Ile Lys Glu Asp Arg Thr Thr Val Val Cys Pro
             35                  40

<210> SEQ ID NO 12
<211> LENGTH: 57
<212> TYPE: PRT
<213> ORGANISM: Artificial Sequence
<220> FEATURE:
<223> OTHER INFORMATION: Consensus amino acid sequence

<400> SEQUENCE: 12

Ile Ser Gly Ala Cys Phe Ala Val Arg Lys Ser Val Phe Thr Lys Val
  1               5                  10                  15
```

-continued

```
Gly Met Phe Asp Glu Gln Met Phe Leu Tyr Gly Glu Arg Met Leu
             20                  25                  30

His Tyr Lys Ile Leu Arg Leu Gly Asn Tyr His Ile Val Tyr Asp Ser
         35                  40                  45

Thr Ile Gly Tyr Leu His Pro Lys Glu
     50                  55

<210> SEQ ID NO 13
<211> LENGTH: 88
<212> TYPE: PRT
<213> ORGANISM: Artificial Sequence
<220> FEATURE:
<223> OTHER INFORMATION: Consensus amino acid sequence

<400> SEQUENCE: 13

Ser Val Val Ile Val Thr Phe Asn Ser Glu Asn Leu Ile Met Asp Cys
  1               5                  10                  15

Leu Asp Ser Ile Phe Lys Tyr Asn Asp Ile Ser Asp Asp Leu Glu Val
             20                  25                  30

Val Leu Val Asp Asn Cys Ser Lys Asn Tyr Leu Ser Met Phe Gly Ser
         35                  40                  45

Ile Glu Glu Lys Tyr Gly Asn Lys Val Val Leu Ile Asn Asn Lys Val
     50                  55                  60

Asn Gly Gly Tyr Gly Gln Gly Asn Asn Leu Gly Val Glu Val Ala Lys
 65                  70                  75                  80

Ala Pro Ile Ile Leu Ile Met Asn
                 85

<210> SEQ ID NO 14
<211> LENGTH: 36
<212> TYPE: PRT
<213> ORGANISM: Artificial Sequence
<220> FEATURE:
<223> OTHER INFORMATION: Consensus amino acid sequence

<400> SEQUENCE: 14

Tyr Asp Ser Thr Ile Gly Tyr Leu His Pro Lys Glu Asn Arg Glu Phe
  1               5                  10                  15

Ser Ser Lys Asn Phe Leu Leu Gly Tyr His Ser Phe Ile Tyr Thr Cys
             20                  25                  30

Asp Lys Leu Gly
         35
```